(12) United States Patent
Hansen

(10) Patent No.: US 10,876,992 B2
(45) Date of Patent: Dec. 29, 2020

(54) WICKING CHANNELS

(71) Applicant: Honeywell International Inc., Charlotte, NC (US)

(72) Inventor: Neils Hansen, Poole (GB)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 239 days.

(21) Appl. No.: 15/877,178

(22) Filed: Jan. 22, 2018

(65) Prior Publication Data

US 2018/0143157 A1  May 24, 2018

Related U.S. Application Data

(63) Continuation of application No. PCT/US2016/036684, filed on Jun. 9, 2016, which is
(Continued)

(51) Int. Cl.
| | |
|---|---|
| *G01N 27/407* | (2006.01) |
| *G01N 27/413* | (2006.01) |
| *G01N 33/00* | (2006.01) |
| *G01N 27/404* | (2006.01) |
| *G01N 27/406* | (2006.01) |
| *H01M 4/02* | (2006.01) |
| *H01M 2/04* | (2006.01) |

(52) U.S. Cl.
CPC ....... *G01N 27/4072* (2013.01); *G01N 27/404* (2013.01); *G01N 27/4045* (2013.01); *G01N 27/413* (2013.01); *G01N 33/0009* (2013.01); *H01M 2/04* (2013.01); *H01M 4/02* (2013.01); *G01N 27/406* (2013.01)

(58) Field of Classification Search
CPC ............. G01N 27/404; G01N 27/4072; G01N 27/413; G01N 33/0009; G01N 27/4045; G01N 27/406
See application file for complete search history.

(56) References Cited

U.S. PATENT DOCUMENTS

| | | |
|---|---|---|
| 3,629,936 A | 12/1971 | Harnoncourt |
| 3,785,948 A | 1/1974 | Hitchman et al. |
| | (Continued) | |

FOREIGN PATENT DOCUMENTS

| | | |
|---|---|---|
| CN | 102818831 A | 12/2012 |
| EP | 0763730 A1 | 3/1997 |
| | (Continued) | |

OTHER PUBLICATIONS

Examination Report for European Application No. 16732822.8, dated Nov. 29, 2019.
Office Action for U.S. Appl. No. 15/877,195, dated Feb. 6, 2020, 28 pages.
Restriction Requirement for U.S. Appl. No. 15/877,195, dated Oct. 30, 2019, 6 pages.
(Continued)

*Primary Examiner* — Ciel P Contreras
(74) *Attorney, Agent, or Firm* — Alston & Bird LLP

(57) ABSTRACT

Embodiments of the disclosure include an electrochemical sensor comprising a housing defining a reservoir; a sensing electrode; a counter electrode; at least one separator retaining an electrolyte, wherein the electrolyte provides an ionically conductive pathway between each of the sensing electrode and the counter electrode within the housing; and a plurality of channels located on the interior of the reservoir, operable to transport electrolyte from the reservoir into the separator.

18 Claims, 18 Drawing Sheets

Related U.S. Application Data a continuation-in-part of application No. PCT/US2015/046461, filed on Aug. 24, 2015, and a continuation-in-part of application No. PCT/US2015/041449, filed on Jul. 22, 2015.

(56) References Cited

U.S. PATENT DOCUMENTS

| | | | |
|---|---|---|---|
| 4,322,278 | A | 3/1982 | Cromer |
| 4,329,214 | A | 5/1982 | Spritzer et al. |
| 4,406,770 | A | 9/1983 | Chan et al. |
| 4,428,817 | A | 1/1984 | Isenberg |
| 4,605,604 | A | 8/1986 | Pollack et al. |
| 4,695,361 | A | 9/1987 | Grady |
| 5,338,429 | A | 8/1994 | Jolson et al. |
| 5,623,875 | A * | 4/1997 | Perets ............... B41K 1/40 101/104 |
| 5,723,036 | A | 3/1998 | Chrzan et al. |
| 5,865,973 | A | 2/1999 | Kiesele et al. |
| 5,914,019 | A | 6/1999 | Dodgson et al. |
| 5,932,079 | A | 8/1999 | Haupt et al. |
| 6,248,224 | B1 | 6/2001 | Kitzelmann |
| 6,454,923 | B1 | 9/2002 | Dodgson et al. |
| 6,666,963 | B1 | 12/2003 | Peng et al. |
| 7,022,213 | B1 | 4/2006 | Austen et al. |
| 7,077,938 | B1 | 7/2006 | Austen et al. |
| 7,935,234 | B2 | 5/2011 | Mett |
| 8,083,914 | B2 | 12/2011 | Millar et al. |
| 8,163,165 | B2 | 4/2012 | Offenbacher et al. |
| 8,632,665 | B2 | 1/2014 | Eckhardt et al. |
| 8,840,765 | B2 | 9/2014 | Offenbacher |
| 2003/0150725 | A1 | 8/2003 | Tschuncky |
| 2005/0034987 | A1 | 2/2005 | Zhou et al. |
| 2005/0145494 | A1 | 7/2005 | Inoue et al. |
| 2006/0021873 | A1 | 2/2006 | Mett |
| 2006/0177350 | A1 * | 8/2006 | Sano ............... B01D 57/02 422/400 |
| 2006/0196770 | A1 | 9/2006 | Tomohiro et al. |
| 2006/0266647 | A1 | 11/2006 | Khalafpour et al. |
| 2007/0187241 | A1 | 8/2007 | Herbert |
| 2008/0202929 | A1 | 8/2008 | Chapples et al. |
| 2009/0288962 | A1 | 11/2009 | Yantasee et al. |
| 2010/0170795 | A1 | 7/2010 | Cowburn et al. |
| 2010/0276287 | A1 * | 11/2010 | Manoukian ......... G01N 27/404 204/412 |
| 2011/0100811 | A1 | 5/2011 | Eckhardt et al. |
| 2011/0100814 | A1 | 5/2011 | Brown et al. |
| 2014/0311905 | A1 | 10/2014 | Stetter et al. |
| 2015/0241382 | A1 | 8/2015 | Mett et al. |

FOREIGN PATENT DOCUMENTS

| | | | |
|---|---|---|---|
| EP | 0780686 | A1 | 6/1997 |
| EP | 1688736 | A1 | 8/2006 |
| EP | 1832873 | A1 | 9/2007 |
| GB | 2332528 | A | 6/1999 |
| GB | 2371873 | A | 8/2002 |
| WO | 0114864 | A2 | 3/2001 |
| WO | 0114868 | A2 | 3/2001 |
| WO | 0131326 | A1 | 5/2001 |
| WO | 02073177 | A2 | 9/2002 |
| WO | 2007115801 | A1 | 10/2007 |
| WO | 2009138357 | A1 | 11/2009 |
| WO | 2017014764 | A1 | 1/2017 |
| WO | 2017014850 | A1 | 1/2017 |
| WO | 2017014851 | A1 | 1/2017 |
| WO | 2017014852 | A1 | 1/2017 |
| WO | 2017014853 | A1 | 1/2017 |
| WO | 2017014854 | A1 | 1/2017 |
| WO | 2017034535 | A1 | 3/2017 |

OTHER PUBLICATIONS

International Application No. PCT/US2015/041449, International Search Report, dated Mar. 24, 2016, 4 pages.
International Application No. PCT/US2015/041449, Written Opinion of the International Searching Authority, dated Mar. 24, 2016, 9 pages.
International Application No. PCT/US2016/036727, International Search Report, dated Aug. 22, 2016, 5 pages.
International Application No. PCT/US2016/036727, Written Opinion of the International Searching Authority, dated Aug. 22, 2016, 7 pages.
International Application No. PCT/US2015/046461, International Search Report, dated Apr. 29, 2016, 3 pages.
International Application No. PCT/US2015/046461, Written Opinion of the International Searching Authority, dated Apr. 29, 2016, 8 pages.
International Application No. PCT/US2016/036637, International Search Report, dated Aug. 22, 2016, 5 pages.
International Application No. PCT/US2016/036637, Written Opinion of the International Searching Authority, dated Aug. 22, 2016, 6 pages.
International Application No. PCT/US2016/036609, International Search Report, dated Aug. 25, 2016, 5 pages.
International Application No. PCT/US2016/036609, Written Opinion of the International Searching Authority, dated Aug. 25, 2016, 7 pages.
International Application No. PCT/US2016/036660, International Search Report, dated Aug. 22, 2016, 5 pages.
International Application No. PCT/US2016/036660, Written Opinion of the International Searching Authority, dated Aug. 22, 2016, 7 pages.
International Application No. PCT/US2016/036684, International Search Report, dated Aug. 10, 2016, 4 pages.
International Application No. PCT/US2016/036684, Written Opinion of the International Searching Authority, dated Aug. 10, 2016, 7 pages.
International Application No. PCT/US2015/041449, International Preliminary Report on Patentability, dated Jan. 23, 2018, 10 pages.
International Application No. PCT/US2015/046461, International Preliminary Report on Patentability, dated Feb. 27, 2018, 9 pages.
International Application No. PCT/US2016/036727, International Preliminary Report on Patentability, dated Jan. 23, 2018, 8 pages.
International Application No. PCT/US2016/036609, International Preliminary Report on Patentability, dated Jan. 23, 2018, 8 pages.
International Application No. PCT/US2016/036637, International Preliminary Report on Patentability, dated Jan. 23, 2018, 7 pages.
International Application No. PCT/US2016/036660, International Preliminary Report on Patentability, dated Jan. 23, 2018, 8 pages.
International Application No. PCT/US2016/036684, International Preliminary Report on Patentability, dated Jan. 23, 2018, 8 pages.
Europe Application No. 16732827.7, Communication pursuant to Rule 161(1) and 162 EPC, dated Mar. 1, 2018, 3 pages.
Europe Application No. 16732818.6, Communication pursuant to Rule 161(1) and 162 EPC, dated Mar. 1, 2018, 3 pages.
Europe Application No. 16732107.4, Communication pursuant to Rule 161(1) and 162 EPC, dated Mar. 1, 2018, 3 pages.
Europe Application No. 16732822.8, Communication pursuant to Rule 161(1) and 162 EPC, dated Mar. 1, 2018, 3 pages.
Communication pursuant to Article 94(3) for European Application No. 16730981.4, dated Oct. 7, 2019, 2 pages.
Office Action for Chinese Application No. 201680055273.3, dated Jul. 26, 2019, 19 pages.
Office Action for Chinese Patent Application No. 201680055273.3, dated Mar. 19, 2020, 12 pages.

* cited by examiner

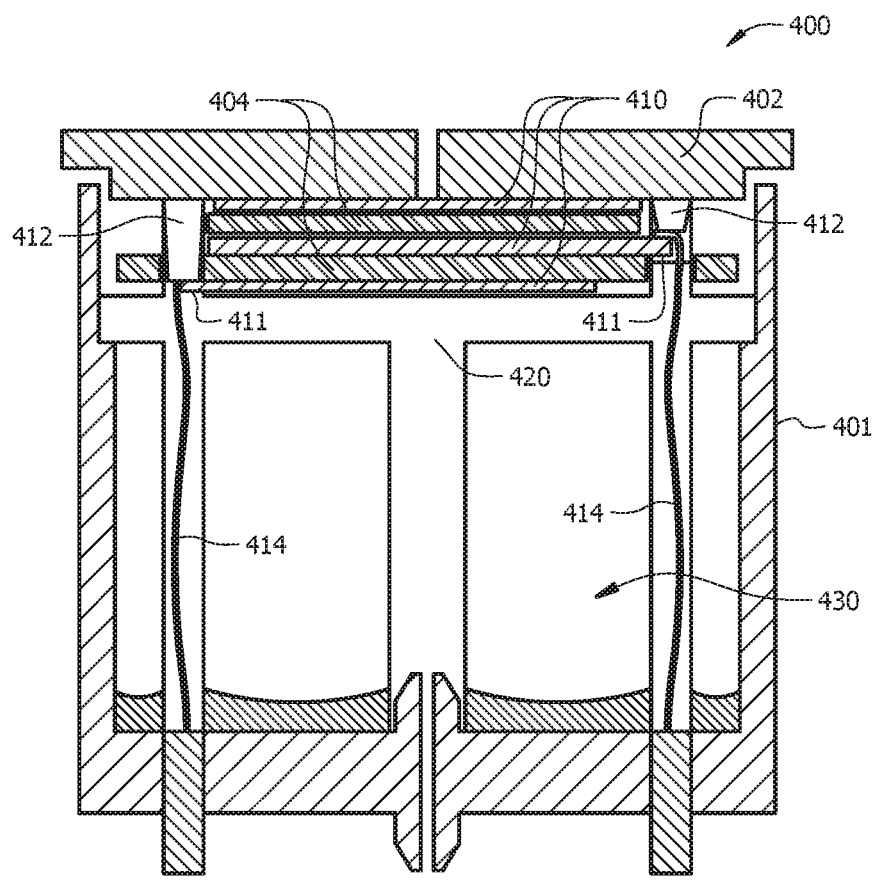
FIG. 4
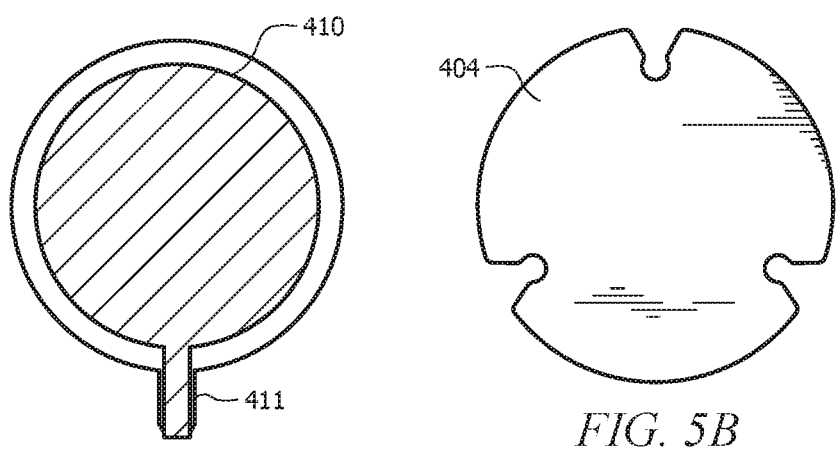
FIG. 5A
FIG. 5B

WICKING CHANNELS

CROSS-REFERENCE TO RELATED APPLICATIONS

This application claims priority to and is a continuation of PCT Patent Application Serial No. PCT/US2016/036684 filed on Jun. 9, 2016 and entitled "Wicking Channels", which is a continuation-in-part of both: 1) PCT Patent Application Serial No. PCT/US15/41449 entitled "Inert Corrosion Barriers for Current Collector Protection", filed 22 Jul. 2015, and 2) PCT Patent Application Serial No. PCT/US15/46461 entitled "Sensing Electrode Oxygen Control in an Oxygen Sensor", filed 24 Aug. 2015, all of which are incorporated herein by reference.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Electrochemical gas sensors generally comprise electrodes in contact with an electrolyte for detecting a gas concentration. The electrodes are electrically coupled to an external circuit though lead wires that are coupled to connector pins. When a gas contacts the electrolyte and the electrodes, a reaction can occur that can create a potential difference between the electrodes or cause a current to flow between the electrodes. The resulting signal can be correlated with a gas concentration in the environment.

In some instances, the sensors can be used to detect a concentration of oxygen in an environment adjacent to the sensor over a range of environmental conditions. Electrochemical sensors such as oxygen sensors can experience a number of issues during operation. For example, when the sensor operates at a certain temperature, a concentration of a target gas, or a reaction product formed by the oxidation or reduction of a target gas, can be dissolved in the electrolyte within the sensor. As the temperature increases, the solubility of most gases, including oxygen and nitrogen, can decrease and result in the formation of bubbles of the gas or gases. In an oxygen sensor, these small bubbles of air containing a mixture of nitrogen and oxygen may diffuse to the sensing electrode and cause instability in the signal at the sensing electrodes, where the oxygen may react by a process of electrochemical reduction at the catalyst surface, resulting in a temporary or transient artificially high oxygen reading as the finite volume of oxygen gas is consumed at the sensing electrode. Other issues, including the availability of electrolyte in contact with the electrodes and issues with corrosion, can also be present. The presence of bubbles of even an inert gas such as nitrogen within the sensor can also be a problem as they may create an easy gas phase path through which oxygen can rapidly diffuse and get to the sensing electrode.

SUMMARY

Embodiments of the disclosure include an electrochemical sensor comprising a housing defining a reservoir; a sensing electrode; a counter electrode; at least one separator retaining an electrolyte, wherein the electrolyte provides an ionically conductive pathway between each of the sensing electrode and the counter electrode within the housing; and a plurality of channels located on the interior of the reservoir, operable to transport electrolyte from the reservoir into the separator.

Embodiments of the disclosure include a method for transporting electrolyte within an electrochemical sensor comprising providing a housing defining a reservoir; forming channels on the interior walls of the reservoir, wherein the channels are small enough to create a capillary effect within the channels; and placing liquid electrolyte within the reservoir, wherein the channels transport the liquid electrolyte through the reservoir toward a separator within the electrochemical sensor.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

FIG. 4 illustrates a cross-sectional view of an electrochemical gas sensor according to an embodiment, where the electrochemical gas sensor comprises a stacked arrangement.

FIGS. 5A-5B illustrate an electrode and a separator for use with an electrochemical gas sensor according to an embodiment.

DETAILED DESCRIPTION

Figure 1:
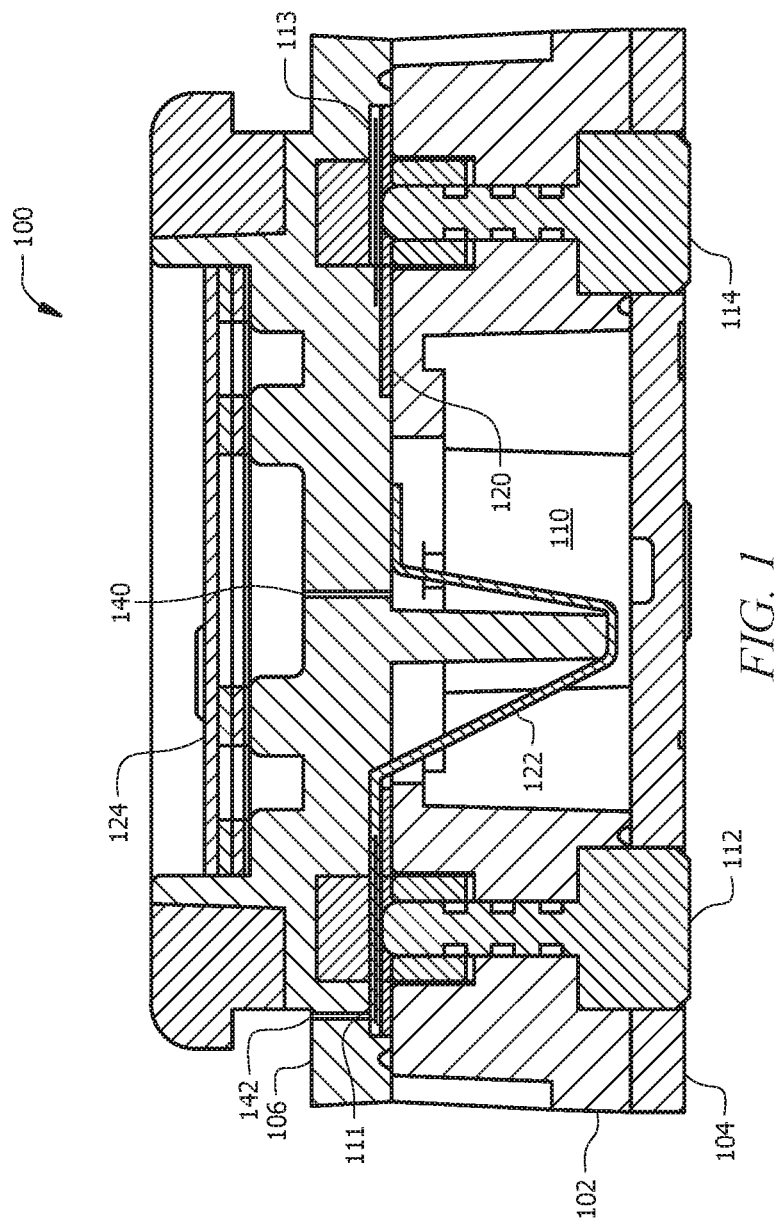
FIG. 1 illustrates a schematic cross section of an embodiment of an electrochemical gas sensor according to an embodiment.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Described herein are various designs and configurations for electrochemical sensors. Electrochemical gas sensors generally detect the presence of a gas in the atmosphere adjacent the sensor by allowing a controlled flow (or diffusion) rate of the ambient gases to enter and react within the sensor. The composition of the electrodes and electrolyte within the sensor can be selected to react with different gases, thereby enabling a degree of selectivity in determining the ambient concentration of a targeted gas. The electrochemical sensors can comprise components and electronic instrumentation (e.g., electronic circuitry such as potential meters, current meters, potentiostats, and the like) that collectively are capable of detecting gases or vapors that are susceptible to electrochemical oxidation or reduction at the sensing electrode, such as carbon monoxide, hydrogen sulphide, sulphur dioxide, nitric oxide, nitrogen dioxide, chlorine, hydrogen, hydrogen cyanide, hydrogen chloride, ozone, ethylene oxide, hydrides, and/or oxygen. While some embodiments described herein refer to an oxygen sensor, the same configurations and methods can be used with the appropriate materials to perform electrochemical oxidation and/or reduction to enable detection of any suitable target gas.

In some aspects, the electrochemical sensors described herein may comprise an oxygen sensor which relies upon the principle of an oxygen pump. In this type of sensor, oxygen is reduced at the sensing electrode and water is oxidized at the counter electrode according to the following half reactions:

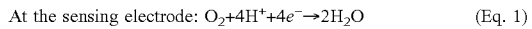

At the sensing electrode: $O_2 + 4H^+ + 4e^- \rightarrow 2H_2O$     (Eq. 1)

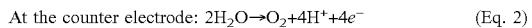

At the counter electrode: $2H_2O \rightarrow O_2 + 4H^+ + 4e^-$     (Eq. 2)

The overall reaction results in the consumption of oxygen at the sensing electrode with an equivalent production of oxygen at the counter electrode. The overall reaction is maintained by means of a reference electrode and a potentiostat, which drive the sensing electrode to a potential which allows the reaction to proceed. The resulting current between the sensing electrode and the counter electrode is proportional to the oxygen concentration of the ambient gas. As embodied by Fick's Law, this proportionality applies for sensors operating under diffusion limited gas access of the capillary and full consumption of the target gas at the sensing electrode. In contrast to other sensors, there is no consuming reaction in which the electrodes or the electrolyte themselves are consumed.

Described herein are a number of features for use with an oxygen sensor that can contribute to the operation of the sensor. In an aspect of the present sensor, contact between an electrode material and an electrical lead can be maintained over a limited area of the sensor. This may allow the separator in contact with the electrode to be separately compressed, generally at a lower compression level than that of the electrical lead. This may allow the separator that acts to retain the electrolyte in contact with the electrode to avoid being over-compressed, which can limit the amount of available electrolyte in contact with the electrode. Also, limiting the compression to the contact between the electrode and electrical lead could even remove the need for a separator at all, if the electrolyte is operable to wet the materials in the sensor sufficiently to remain in contact with them (e.g. ionic liquids). At the same time, adequate compression between the electrode and the electrical lead may be maintained so that the electrical connection between the electrical lead and the electrode is maintained.

In an aspect of the present sensor, the result of the reactions at each electrode is an oxygen concentration gradient in the electrolyte. The concentration of the dissolved oxygen in the electrolyte varies with the composition of the electrolyte, the temperature of the electrolyte, the atmospheric pressure, and the position relative to the sensing electrode and the counter electrode. The oxygen concentration at or near the sensing electrode may be around 0%, while the oxygen concentration in the electrolyte at or near the counter electrode may correspond to a concentration close to or above the ambient gas concentration. Within this gradient, the dissolved oxygen and/or nitrogen concentration may exceed a saturated concentration due to a temperature rise. As the temperature rises above the saturation concentration, a gas phase comprising oxygen and/or nitrogen can form, and the resulting gas phase bubbles can travel to the sensing electrode where they may react. The resulting spike in the concentration value can result in a false alarm.

In some aspects, the air/electrolyte interface can be controlled so that the closest interface is positioned a suitable distance away from the sensing electrode in order to control the oxygen concentration in the electrolyte surrounding the sensing electrode within the sensor itself. Specifically, a low oxygen zone can be created around the sensing electrode that is substantially sealed off from the air/electrolyte interface. This zone may limit the oxygen introduction to the sensing electrode to that occurring through the wetted separator. In order to control the inlet oxygen diffusion rate, the relative geometric parameters of the separator can be adjusted along with the relative distances between the sensing electrode, the reference electrode, and the counter electrode so that a flux of the oxygen to the sensing electrode is controlled. This may provide an oxygen sensor having an improved resistance to spiking failures across a broad range of temperatures. In some embodiments, a sealed area around the sensing electrode can be used to limit the amount of oxygen reaching the sensing electrode to a liquid-phase diffusional flow, which may be orders of magnitude slower than gas phase diffusional flow. The sealed area may limit or prevent oxygen in a gas from contacting the separator adjacent to the sensing electrode, which may help to avoid any spiking failures.

In other aspects, the interface for the sensing electrode can occur based on gas diffusion through a gas diffusion membrane that is part of the sensing electrode. In this embodiment, the gas can contact the membrane within the sensor and diffuse to the electrode interface to form a three-phase gas/electrolyte/electrode interface for carrying out a reaction, which can produce the signal used to indicate an amount of the gas present.

In some aspects, the separator used with the sensor can be planar, and the use of a specific geometry may allow for various oxygen gradients to be controlled. Various features such as the cross-sectional area along the length of the separator can be controlled through the shape of the separator. In some aspects, various ablation patterns can be used to control a diffusion rate through a portion of the separator. The overall design of the separator may then allow a specific gradient of reactants (e.g., dissolved oxygen, ions, etc.) to be maintained during operation of the sensors.

In an aspect of the sensor, a breather tab can be used to allow gases that collect within the sensor body to be vented. Problems can arise when a liquid electrolyte level within the sensor body covers a breather vent. By limiting the contact between any accumulated gas phase and the breather material, the gas cannot pass through the vent to an exterior of the sensor body. As disclosed herein, a breather tab can be used that passes through the sensor body along an elongated path. The path allows the breather tab to be in contact with the gas phase, and thereby vent gas from the sensor body at a wide variety of electrolyte liquid levels and orientations of the sensor.

In still other aspects, various wicking designs can be used with the sensor to aid in electrolyte transport between an electrolyte reservoir and the separator. The sensor can generally be designed so that the electrolyte is in contact with the separator, which serves as a wick to retain the electrolyte in contact with the electrodes. In some instances (e.g., low electrolyte levels, differing orientations, etc.), the electrolyte may not properly wick into the separator. In order to transport the electrolyte from a reservoir to the separator, wicking channels can be included within the sensor body or housing to further transport the electrolyte to the separator. Various structures such as capillary channels can be formed in one or more portions of the inner surface of the housing. This may serve to wick the electrolyte to the separator at a wide variety of angles and electrolyte levels.

Figure 2:
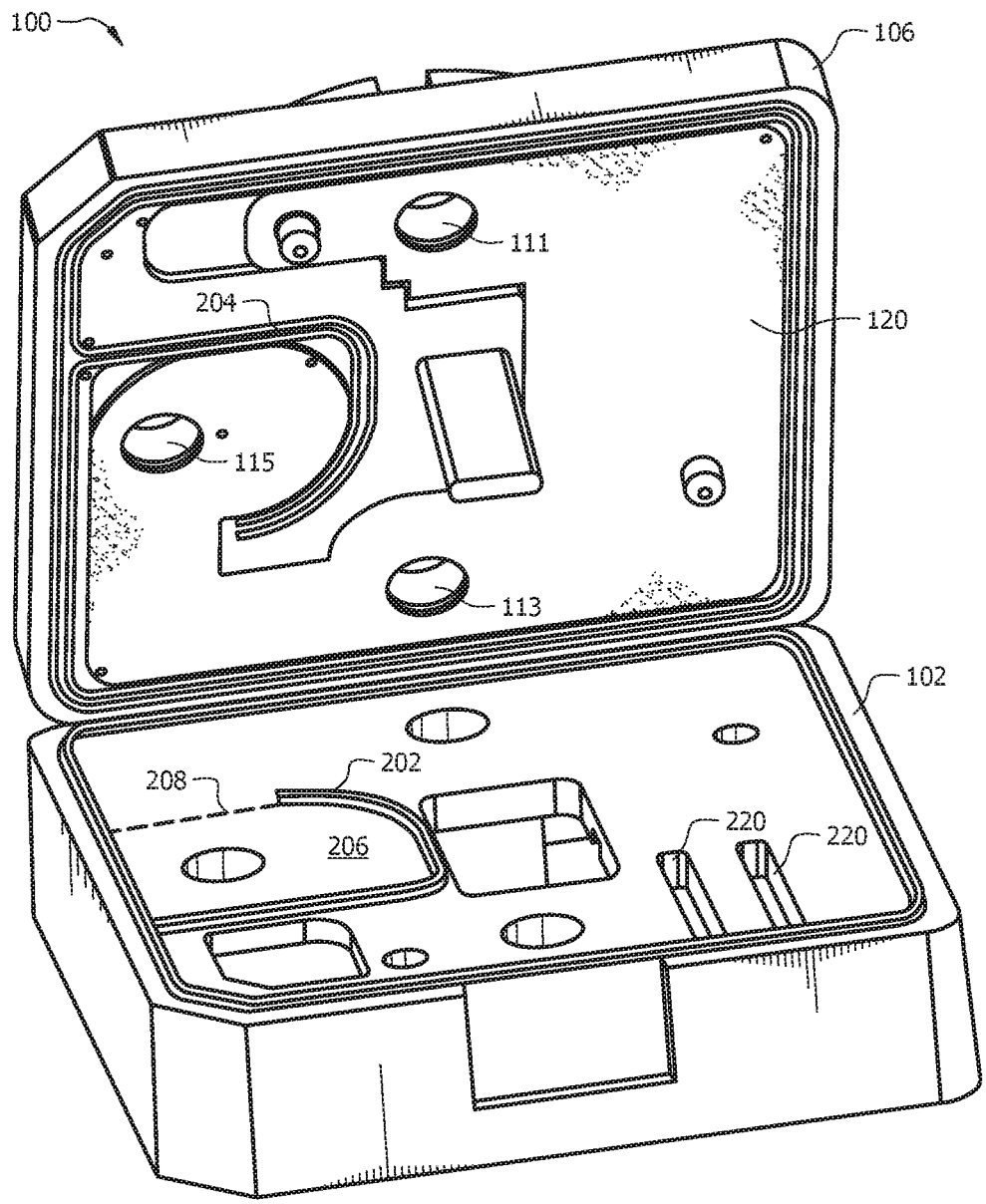
FIG. 2 illustrates an isometric view of the electrochemical sensor according to an embodiment.

FIG. 1 illustrates a cross-section of an embodiment of an electrochemical sensor 100, and FIG. 2 illustrates an isometric view of the electrochemical sensor of FIG. 1 with the layout of the separator and electrodes illustrated. The electrochemical sensor 100 can comprise a multi-part housing including at least a body 102 defining a hollow interior space 110 for receiving and retaining an electrolyte (e.g., forming an electrolyte reservoir), a base 104, and a cap 106. The base 104 and the cap 106 can sealingly engage the body 102 to form an integral unit.

The body 102 may have a generally rectangular or square shape, though other shapes such as cylindrical, oval, oblong, or the like are also possible. The body 102, the cap 106, and the base 104 can all be formed from materials that are inert to the selected electrolyte. For example, the body 102, the cap 106, and/or the base 104 can be formed from one or more plastic or polymeric materials. In an embodiment, the body 102, the cap 106, and/or the base 104 can be formed from a material including, but not limited to, acrylonitrile butadiene styrene (ABS), polyphenylene oxide (PPO), polystyrene (PS), polypropylene (PP), polyethylene (PE) (e.g., high density polyethylene (HDPE)), polyphenylene ether (PPE), or any combination or blend thereof.

One or more openings can be formed through the body to allow the ambient gas to enter the interior space 110 and/or allow any gases generated within the housing to escape. In an embodiment, the electrochemical sensor 100 may comprise at least one inlet opening 140 to allow the ambient gas to enter the housing, and at least one exhaust opening 142 to allow any gases generated by the counter electrode 111 to exhaust from the housing. The inlet opening 140 and/or the exhaust opening 142 can be disposed in the cap 106 when a cap is present and/or in a wall of the body 102. The inlet opening 140 and/or the exhaust opening 142 can comprise a diffusion barrier to restrict the flow of gas (e.g., oxygen) to the sensing electrode 115. The diffusion barrier can be created by forming the inlet opening 140 and/or the exhaust opening 142 as a capillary, and/or a film or membrane can be used to control the mass flow rate through one or more of the openings 140, 142.

The inlet opening 140 and/or the exhaust opening 142 may serve as capillary openings to provide a rate limited exchange of the gases between the interior and exterior of the housing. In an embodiment, the inlet opening 140 may have a diameter between about 20 µm and about 200 µm, where the opening can be formed using a conventional drill for larger openings and a laser drill for smaller openings. The inlet opening 140 may have a length between about 0.5 mm and about 5 mm, depending on the thickness of the cap 106. The exhaust opening 142 may have a diameter and length in the same ranges as the inlet opening 140. In some embodiments, two or more openings may be present for the inlet gases and/or the exhaust gases. When a membrane is used to control the gas flow (or diffusion) into and/or out of the housing, the opening diameter may be larger than the sizes listed above as the film can contribute to and/or may be responsible for controlling the flow rate of the gases into and out of the housing. In general, the gas access between the ambient environment and the interior of the electrochemical sensor 100 is intended to occur through the inlet opening 140. When exhaust opening 142 is present, the exhaust opening 142 can be configured so that the rate of diffusion through the exhaust opening 142 may be less than that through the inlet opening 140, thereby reducing any access through the exhaust opening 142 relative to the inlet opening 140.

A porous membrane (e.g., vent membrane 314 in FIG. 3) can also be disposed within the sensor 100, a portion of which can serve as a vent membrane to allow any gas formed within the sensor to pass through the membrane and out the exhaust opening 142 to the atmosphere. The vent membrane may be porous to a gas, but can generally form a barrier to the passage of any liquids such as the electrolyte solution in order to form a liquid seal relative to the outside environment. In an embodiment, the vent membrane can be formed from polytetrafluoroethylene (PTFE), fluorinated ethylene propylene (FEP), polyethylene (PE), polypropylene (PP), polymethyl methacrylate (PMMA), polyethylene terephthalate (PET) polyaryletheretherketone (PEEK), perfluoroalkoxy (PFA), ethylene chlorotrifluoroethylene (E-CTFE), and any combination thereof. The vent membrane can cover the exhaust opening 142, and in some aspects can be sealed around the vent to prevent fluid leakage from the interior of the sensor through the exhaust opening 142. The flow rate of the gas between the reservoir 110 and the vent membrane covering the exhaust opening 142 can be controlled by the relative permeability of the vent membrane to selected gases.

A porous membrane 122 can also be disposed within the sensor 100, a portion of which can serve as a breather tab to allow any gas forming within the sensor to pass through the membrane to the vent membrane. In some embodiments, the porous membrane 122 can serve as a vent membrane over the exhaust opening 142. The porous membrane 122 may be porous to a gas, but can generally form a barrier to the passage of any liquids such as the electrolyte solution in order to allow any gas to pass through the porous membrane 122 to the vent membrane and/or the exhaust opening 142. In an embodiment, the porous membrane 122 can be formed from polytetrafluoroethylene (PTFE), fluorinated ethylene propylene (FEP), polyethylene (PE), polypropylene (PP), polymethyl methacrylate (PMMA), polyethylene terephthalate (PET) polyaryletheretherketone (PEEK), perfluoroalkoxy (PFA), ethylene chlorotrifluoroethylene (E-CTFE), and any combination thereof. The porous membrane 122 can cover the exhaust opening 142. The flow rate of the gas between the reservoir 110 and the porous membrane 122 can then be controlled by the relative permeability of the porous membrane 122 to selected gases. When the vent membrane is present, the porous membrane 122 may have a higher gas permeability to allow the gases within the sensor 100 to pass to the vent membrane.

A higher density, lower porosity bulk flow membrane 124 can be disposed within the cap 106 to serve as a barrier to the bulk flow of gases into the sensor 100 while allowing for relatively free diffusion of gas through the bulk flow membrane 124, which can impart tolerance to local environmental pressure changes that can disrupt the diffusion controlled operation of the inlet opening 140. The inlet opening 140 through the cap 106 and/or the bulk flow membrane 124 may provide a restrictive and/or tortuous diffusional path to allow the gases in the atmosphere to pass into the sensor 100 to react with the electrodes and electrolyte solution at a flowrate that does not cause undesirable sensor response characteristics, which can manifest as significant increased responses over an extended period such as minutes to hours depending upon the magnitude of the bulk flow gas volume that diffused through the capillary.

The inlet opening 140 may provide an opening into the central space within the housing. The resulting incoming gases (e.g., including the target gas) may contact the electrolyte, for example, within the separator 120. In an embodiment, the exhaust opening 142 can be disposed adjacent to the counter electrode 111 and can serve to allow gases generated at the counter electrode 111 to escape from the housing so that the gases do not accumulate within the housing and create false readings by flowing to the sensing electrode 115.

It can be useful to minimize the parts count in the sensor design due to the implications for cost and complexity of manufacture and reproducibility of assembly. It can also be advantageous during the assembly of the sensors to use full or partial automation when there are fewer parts to handle. There is a constraint within most instrument designs that the gas access must be on the upper x-y plane due to the need to allow clear gas access while the instrument is being held in the hand with the display clearly visible. This constrains many of the geometrical options for the designer. One aspect of the design which helps to meet this requirement is the cap section, and in particular, the portion of the cap 106 containing the inlet opening 140. This is designed to be located in the outer shell of the instrument. In this way, the internal sensor volume can be created in a region which would normally be left as a void in traditional sensors. In some aspects, the cap can contain various elements such as the filter, bulk flow membrane, and inlet opening.

Within the electrochemical gas sensor 100, a separator 120 may be disposed between the body 102 and the cap 106. The separator 120 can comprise a porous member that acts as a wick for the retention and transport of the electrolyte between the reservoir and the electrodes. In general, the separator 120 is electrically insulating to prevent a direct electrical connection between the electrodes through the separator material itself (e.g., as opposed to through the electrolyte). In an embodiment of the separator, the separator may comprise high volume, non-woven separator materials such as a porous felt and/or a non-woven, unbound, glass fiber separator material described as Whatman GFA separator. This typical separator material is manufactured in roll form where the glass density (or "grammage") is nominally uniform along and across the roll. The separator 120 can comprise a woven porous material, a porous polymer (e.g., an open cell foam, a solid porous plastic, etc.), or the like, and is generally chemically inert with respect to the electrolyte and the materials forming the electrodes. In an embodiment, the separator 120 can be formed from various materials that are substantially chemically inert to the electrolyte including, but not limited to, glass (e.g., a glass mat), polymer (plastic discs), ceramics, or the like.

In some aspects, the electrolyte can comprise an aqueous electrolyte, an ionic liquid, a solid electrolyte, and/or a liquid non-aqueous, non-ionic additive. In an aspect, the electrolyte can comprise any aqueous electrolyte such as an aqueous solution of a salt, an acid, or a base depending on the target gas of interest. In an embodiment, the electrolyte can comprise a hygroscopic acid such as sulfuric acid for use in an oxygen sensor. Other target gases may use the same or different electrolyte compositions. In addition to aqueous electrolytes, ionic liquid electrolytes can also be used to detect certain gases. The electrolyte can be maintained within the sensor 100 to allow the reactions to occur at the sensing electrode 115 and the counter electrode 111. In some embodiments the electrolyte can comprise a non-ionic, non-aqueous fluid, gel, or solid, which can be appropriately doped to provide the ionic characteristics to the electrolyte. In an embodiment, the electrolyte can be a liquid that is maintained in the separator 120, which acts as an absorbent medium to retain the electrolyte in contact with the electrodes. In some embodiments, the electrolyte can be present in the form of a gel. In an embodiment, the electrolyte may comprise a carrier or other additive, such as poly(ethylene glycol), poly(ethylene oxide), poly(propylene carbonate).

In an embodiment, the electrolyte can comprise a solid electrolyte. Solid electrolytes can include electrolytes adsorbed or absorbed into a solid structure such as a solid porous material and/or materials that allow protonic and or electronic conduction as formed. In an embodiment, the solid electrolyte can be a protonic conductive electrolyte membrane. The solid electrolyte can be a perfluorinated ion-exchange polymer such as Nafion. Nafion is a hydrated copolymer of polytretafluoroethylene and polysulfonyl fluoride vinyl ether containing pendant sulfuric acid groups. When used, a Nafion membrane can optionally be treated with an acid such as $H_3PO_4$, sulfuric acid, or the like, which improves the moisture retention characteristics of Nafion and the conductivity of hydrogen ions through the Nafion membrane. The sensing, counter and reference electrodes can be hot-pressed onto the Nafion membrane to provide a high conductivity between the electrodes and the solid electrolyte.

The counter electrode 111, reference electrode 113, and sensing electrode 115 within the electrochemical gas sensor 100 can be electrically connected to an external circuit through one or more electrical connections. In an embodiment, the electrodes 111, 113, 115 may have connector pins 112, 114 extending through the base 104 and/or the body 102 that can be electrically coupled, directly or indirectly, with the electrodes 111, 113, 115. While not shown in FIG. 1, the sensing electrode 115 can have a connector pin disposed through the base 104 to contact the sensing electrode 115. The external surfaces of the connector pins 112, 114 can be electrically coupled to an external circuit. The connector pins 112, 114 may sealingly engage the base 104 and/or the body 102 so that the connector pins 112, 114 are substantially sealed from the interior space 110 of the electrochemical gas sensor 100.

The connector pins 112, 114 can be formed from an electrically conductive material, which may be plated or coated. In an embodiment, the connector pins 112, 114 can be formed from brass, nickel, copper, or the like. The connector pins 112, 114 can be coated to reduce degradation due to the contact with the electrolyte. For example, the connector pins 112, 114 can include a coating of precious metal such as gold, platinum, silver, or the like, other base metals such as tin, or other metals such as niobium and tantalum. In an embodiment of an electrochemical sensor, the pins may comprise gold flash plated, nickel coated brass pins.

In some aspects, the connector pins 112, 114 can contact the electrode directly, through a conductive layer, and/or one or more current collectors such as a metal wire or conductive ribbon can be used to conduct electrical charges generated at active electrode surfaces to the connector pins 112, 114, which tend to be more robust than the metal wire or ribbon. When current collectors are used, the connector pins 112, 114 can facilitate connection between the current collectors and an external electronic circuit.

The external circuitry can be used to detect a current between the sensing electrode 115 and the counter electrode 111 to determine the target gas concentration in an ambient gas in contact with the sensor 100. A potentiostatic circuit can be used to maintain the potential of the sensing electrode 115 at a predetermined value relative to the reference electrode 113 independently from the counter electrode 111, whose potential remains uncontrolled and limited only by the electrocatalytic properties of the electrode. In an embodiment, the potential of the sensing electrode 115 relative to the reference electrode 113 can be set at a value of between about −300 and −800 mV for the electrochemical sensor 100 when the target gas is oxygen. In some embodiments, the sensing electrode 115 and the reference electrode 113 may comprise platinum when the potential of the sensing electrode 115 relative to the reference electrode 113 is set at a value of between about −300 and −800 mV for the electrochemical sensor 100 when the sensing gas is oxygen.

The electrodes 111, 113, 115 generally allow for various reactions to take place to allow a current or potential to develop in response to the presence of a target gas such as oxygen. The resulting signal may then allow for the concentration of the target gas to be determined. The electrodes 111, 113, 115 can comprise a reactive material suitable for carrying out a desired reaction. For example, the electrodes 111, 113, 115 can be formed of a mixture of electrically conductive catalyst particles in a binder such as polytetrafluoroethylene (PTFE). For an oxygen sensor, an exemplary electrode can comprise carbon (e.g., graphite) and/or one or more metals or metal oxides such as copper, silver, gold, nickel, palladium, platinum, ruthenium, iridium and/or oxides of these metals. The catalyst used can be a pure metal powder, a metal powder combined with carbon, a metal powder supported on electrically conductive medium such as carbon, or a combination of two or more metal powders either as a blend or as an alloy. The materials used for the individual electrodes can be the same or different.

The electrode can also comprise a backing material or substrate such as a membrane to support the catalyst mixture. The backing material or substrate can comprise a porous material to provide gas access to the electrode through the substrate. The backing material may also be hydrophobic to prevent the electrolyte from escaping from the housing.

The electrodes can be made by mixing the desired catalyst with a hydrophobic binder such as a PTFE emulsion and depositing the mixture on the backing material. The electrodes might be deposited onto the substrate, by for example, screen printing, filtering in selected areas from a suspension placed onto the substrate, by spray coating, or any other method suitable for producing a patterned deposition of solid material. Deposition might be of a single material or of more than one material sequentially in layers so as, for example, to vary the properties of the electrode material through its thickness or to add a second layer of increased electrical conductivity above or below the layer which is the main site of gas reaction.

When the target gas is oxygen in a sensor using a diffusion limited opening (e.g., a capillary, etc.), the oxygen concentration at the sensing electrode 115 within the sensor results from both the oxygen diffusing to the sensing electrode 115 through the separator 120 as well as oxygen entering the separator 120 as a result of a gas/separator 120 interface at any point along the separator 120 within the sensor 100. When the gas can contact the electrolyte in the separator 120 adjacent to the sensing electrode 115, a substantial portion of the oxygen contacting the sensing electrode 115 can result from the contact between the gas and the electrolyte in the separator 120 adjacent to the sensing electrode 115. This can result in a localized oxygen concentration in the electrolyte that exceeds the saturation concentration or solubility at certain temperatures. A temperature rise could then result in a higher rate of gaseous oxygen diffusion to the active catalyst of the sensing electrode 115, as a direct result of gas evolution from the electrolyte and subsequent contact with the sensing electrode 115 to create a transient "spike" in the output current.

In some aspects, the design of the separator 120 can be used to help prevent spiking failures by designing the separator 120 to provide a pressure resistance to a bubble gas containing oxygen from passing through the separator 120 and reaching the sensing electrode 115 during environmental pressure changes. The separator 120 can be designed so that the pressure resistance is higher than the pressure resistance through the vent, thereby routing the gas through the vent to exit the sensor housing. As an example, pressure changes of up to about 400 millibar can be associated with temperature changes from −40° C. to +60° C. and back again. The separator 120 can be designed to provide a pressure resistance to a gas bubble of at least about 400 millibar, at least about 500 millibar, or at least about 600 millibar.

In order to avoid the potential for spiking in some aspects, the oxygen concentration at or near the sensing electrode 115 can be controlled to a level less than the threshold oxygen solubility at the operational temperature. In general, the dissolved oxygen concentration in the electrolyte at or near (e.g., within several millimeters) the sensing electrode 115 should be as close to zero as possible, thereby ensuring that the majority of the measured sensor response results from the controlled diffusion rate of gaseous oxygen through the capillary gas entry hole, rather than the less controlled, internal diffusion rate of dissolved oxygen through the separator 120. Limiting or preventing the internal diffusion rate of oxygen can improve the correlation between the sensor response and the gaseous oxygen concentration of the external environment. Ideally, the rate at which the oxygen reaches the sensing electrode 115 from the environment in which the oxygen is to be detected should be less than the consumption rate of the oxygen at the sensing electrode 115 (such that the electrode may be diffusion limited over all conditions over the life of the sensor). Typically, for most embodiments of this sensor type, the consumption rate of oxygen at the sensing electrode 115 (e.g., the reduction rate) may be greater than the diffusion rate of gaseous oxygen to the sensing electrode 115 from the environment in which the target gas is to be detected through all openings in the sensor 100. When additional internal diffusion of dissolved and/or gaseous target gas occurs from the electrolyte near the sensing electrode 115, the current generated in the circuit may correlate poorly with the external target gas concentration.

In an embodiment, the threshold may be a saturation concentration at a design temperature. For example, the threshold may be the oxygen saturation concentration in the electrolyte at the upper operating temperature specified for the sensor 100. In some embodiments, the threshold may be a percentage of the saturation concentration at a specified temperature. This may allow for a safety factor to be included in the design of the electrochemical sensor 100. For example, the target gas (e.g., oxygen) concentration may be controlled to less than about 90%, less than about 80%, or less than about 70% of the saturation concentration at a specified temperature.

The target gas concentration at or near the sensing electrode 115 can be controlled in a number of ways including providing a spacing between the counter electrode 111 and the sensing electrode 115, limiting a gas/electrolyte contact at or near the sensing electrode 115, and/or selecting a geometry for the separator 120 retaining the electrolyte to limit the flux of the target gas to the sensing electrode 115 to a rate that is less than a consumption rate of the target gas at the sensing electrode 115 (e.g., a target gas reduction rate at the sensing electrode 115).

In an oxygen sensor, a dissolved target gas concentration gradient can be established in response to the operation of the electrochemical sensor between the counter electrode 111 and the sensing electrode 115 under normal operational conditions. Alternatively, in another sensor such as a CO sensor or even in oxygen sensors having a different configuration, there may be no gradient of target gas within the separator, since CO is not evolved at the counter electrode and the incoming CO from the capillary should be consumed by the sensing electrode 115. In some oxygen sensors, the dissolved target gas concentration gradient may generally be expected to represent a concentration either at, or approaching, the solubility limit of dissolved target gas in the electrolyte surrounding the counter electrode 111 and either low, or approximately zero, concentration of dissolved target gas in the electrolyte around the sensing electrode 115 when the electrochemical sensor 100 is used in typical operational environments. Since the target gas concentration in the electrolyte decreases towards the sensing electrode 115, the creation of a suitable distance between the counter electrode 111 and the sensing electrode 115 can be used to limit the concentration of dissolved target gas in the electrolyte near the sensing electrode 115 to less than the threshold.

In an embodiment, the separation distance can be provided by forming an ionically conductive pathway between the electrodes 111, 113, 115 having a desired length. The sensing electrode 115, the reference electrode 113, and the counter electrode 111 can be disposed on the ionically conductive pathway, with a distance separating each electrode. In an embodiment, the ionically conductive pathway can extend in any direction within the housing in order to achieve a desired spacing. The resulting separation may include a labyrinth configuration so that the ionically conductive pathway is not in a straight line, which would result in an oxygen sensor having relatively large dimensions.

In an embodiment as shown in FIG. 2, the separator 120 can comprise a planar configuration, and each of the electrodes 111, 113, 115 can be disposed in a planar configuration in contact with the electrolyte retained in the separator 120. As shown, the separator 120 may form an ionically conductive pathway, hereafter referred to as a "conductive pathway," by virtue of the electrolyte being retained in the separator 120. The separator 120 can extend in a plane within the housing between the counter electrode 111, the reference electrode 113, and the sensing electrode 115. In this embodiment, each of the electrodes 111, 113, 115 may be disposed in a substantially planar arrangement to contact the electrolyte in the planar separator 120. The conduction pathway may not extend in a straight line within the housing, which may allow the conduction pathway to attain the desired length or separation between the electrodes while maintaining a compact sensor design. While the conduction pathway does not extend in a straight line, a single conduction pathway is formed in which the sensors are arranged in series on the pathway. For example, the middle electrode is disposed between the two end electrodes, and a shorter path is not present between the end electrodes than between either of the end electrodes and the middle electrode.

In an embodiment as shown in FIG. 2, the sensing electrode 115 and the counter electrode 111 can be disposed at the ends of the conduction pathway, and the reference electrode 113 can be disposed between the sensing electrode 115 and the counter electrode 111. This configuration locates the reference electrode 113 at a position where it is subject to relatively steady concentration gradients of dissolved target gas and ions diffusing through the electrolyte, which may reduce the current variations generated by the potentiostatic driver circuitry that manifest as measurement fluctuation or drift. The steady concentration gradients across the reference electrode in this configuration may be considered a more robust design solution for producing a stable reference potential than the highly variable and fluctuating concentrations of protons and dissolved target gas that might be generated across the reference electrode 113 when it is positioned outside of the potential gradient, which can result in increased fluctuation or drift in the circuit.

The distance between the electrodes 111, 113, 115 on the conduction pathway may affect the potential for spiking to occur. In an embodiment, the distance along the conduction pathway (e.g., along a centerline of the conduction pathway) between the counter electrode 111 and the reference electrode 113 may be between about 1 mm and about 20 mm or between about 2 mm and about 15 mm, where the reference electrode 113 is disposed between the counter electrode 111 and the sensing electrode 115. In some embodiments, the distance (e.g., along a centerline of the conduction pathway) between the sensing electrode 115 and the counter electrode 111 may be between about 5 mm and about 30 mm, or between about 7.5 mm and about 25 mm. The relative ratio between the electrodes 111, 113, 115 may also affect the target concentration gradient. In an embodiment, a ratio of a distance between the counter electrode 111 and the reference electrode 113 to a distance between the counter electrode 111 and the sensing electrode 115 can be between about 1:1 and about 1:10, or between about 1:1.5 and about 1:5.

In some embodiments, a diffusion barrier may be provided within the sensor 100 to prevent the cross-diffusion of target gas to the sensing electrode 115. This configuration may allow the conduction pathway to place the sensing electrode 115 relatively close to the counter electrode 111 without any target gas generated at the counter electrode 111 reaching the sensing electrode 115. The use of a diffusion barrier may also allow the separator 120 to be positioned within a compact sensor while providing the separation needed to control the spiking type errors. In some embodiments of the sensor 100, the body 102 may comprise one or more breather slots 220 (described in more detail below).

As shown in FIG. 2, the diffusion barrier can be formed around the sensing electrode 115 while the reference electrode 113 and the counter electrode 111 are disposed outside of the area defined by the diffusion barrier. The diffusion barrier can comprise a seal formed between the cap 106 and the body 102. In an embodiment, the seal can comprise a shoulder 202 formed on the body 102 and/or the cap 106, with a corresponding recess 204 or mating structure on the other component. A compliant material may be disposed on the shoulder 202 and/or the recess 204 to form a seal between the body 102 and the cap 106. The shoulder 202 can be formed from the same material as the body 102 and/or the cap 106, and may comprise an integral structure with the body 102 or the cap 106. The compliant seal, when present, may comprise any impermeable materials that is inert with respect to the electrolyte and has a sufficiently low gas permeation rate to ensure a low dissolved target gas concentration is maintained in the electrolyte around the sensing electrode 115.

When the cap 106 and the body 102 are enclosed, the shoulder 202 may contact the recess 204, and any compliant seal may be positioned there between so that a seal is formed in the area around the sensing electrode 115. In some embodiments, a joining process (e.g., ultrasonic welding, etc.) can be used to fuse the two components to enhance the seal between the body 102 and the cap 106. A similar barrier may be formed around the perimeter of the body 102 and the cap 106 as part of the manufacturing process for the sensor 100 to seal the housing and prevent the electrolyte from leaking.

In some embodiments, a small gap may exist between the shoulder 202 and the recess 204, or at an edge of the joint between the shoulder 202 and the recess 204. When the material of the shoulder 202 and the recess 204 are hydrophilic, a small amount of the electrolyte may be retained in the gap due to capillary action, resulting in a layer of the electrolyte being maintained at the seal between the cap 106 and the body 102. The relatively small gap size along with the electrolyte disposed in the gap may form a diffusion barrier that has a greater diffusional resistance than the separator 120, thereby effectively limiting the diffusion of any gas through the chamber edge as compared to the diffusional path through the separator 120.

When the body 102 and the cap 106 are engaged, a chamber 206 can be formed by an inner surface of the body 102, an inner surface of the cap 106, and the inner surface of the shoulder 202. The edge seal may also define a surface of the chamber 206. The chamber 206 may have an opening 208 through which the separator 120 retaining the electrolyte can extend. Within the chamber 206, the separator 120 may be positioned to maintain contact between the electrolyte and the sensing electrode 115. The separator 120 retaining the electrolyte may substantially fill the opening 208 so that any gas within the sensor 100 is substantially prevented from entering the chamber 206 through a convective flow.

When the separator 120 substantially fills the opening 208, the target gas reaching the sensing electrode 115 may originate from target gas diffusing through the electrolyte retained in the separator 120 from outside of the chamber 206, for example, as resulting from a gas/electrolyte interface outside of the chamber 206. The distance between the opening 208 and the sensing electrode 115 may be small compared to the conduction pathway length between the counter electrode 111 and the sensing electrode 115. In an embodiment, the portion of the separator 120 contained within the chamber 206 may be configured to provide a target gas concentration within the electrolyte within the separator 120 corresponding to less than about a 1%, less than about a 0.8%, less than about a 0.6%, less than about a 0.4%, less than about a 0.2%, or less than about a 0.1% target gas concentration at the sensing electrode 115. In an embodiment, the distance between the opening 208 and the sensing electrode 115 may be between about 0.1 mm and about 4 mm, or between about 0.5 mm and about 1.5 mm. A similar distance may be provided around the sensing electrode 115 within the chamber 206 in the event that any target gas is able to enter the chamber 206 through the seal.

The positioning of the sensing electrode 115 within the chamber 206 may limit the area of the gas/electrolyte interface and reduce or prevent a gas/electrolyte interface within the chamber 206, which can limit the potential for creating a high target gas concentration at or near the sensing electrode 115. Rather, any target gas diffusing to the sensing electrode 115 must diffuse through the electrolyte in the separator 120 over a short distance between the exterior of the chamber 206 and the sensing electrode 115 within the chamber 206. The resulting zone of decreased target gas concentration within the electrolyte may help limit the potential for the target gas concentration to exceed a saturation concentration in the electrolyte within the chamber 206. Any gas evolving due to a temperature rise may then be prevented from reaching the sensing electrode 115 except through the electrolyte in the separator 120.

In any of the embodiments described herein, the geometry of the separator 120 may affect the flux of target gas to the sensing electrode 115 through the electrolyte in the separator 120, and the geometry can be selected so that the rate of target gas diffusion to the sensing electrode 115 is less than a consumption rate of target gas at the sensing electrode 115 (e.g., an oxygen reduction rate at the sensing electrode 115). The thickness of the separator 120 (e.g., a distance perpendicular to the plane of the separator 120) near the chamber 206 may be determined by the available distance between the cap 106 and the body 102 when the sensor is assembled. In an embodiment, the separator 120 may contact both the cap 106 and the body 102. In some embodiments, the thickness of the separator 120 may be between about 0.5 mm and about 5 mm. The width of the separator 120 at the opening 208 may be based on a total area available for the diffusion of target gas into the chamber 206 through the electrolyte retained in the pores of the separator 120. In general, the area for diffusion (e.g., the product of the width times the thickness along with the porosity of the separator 120) may affect the total amount of target gas diffusing into the chamber 206 through the electrolyte to contact the sensing electrode 115. In some embodiments, the width of the separator 120 at the opening 208 may be between about 0.5 mm and about 20 mm, between about 5 mm and about 17 mm, or between about 6 mm and about 15 mm. The selection of the material for the separator 120, the selection of the electrolyte and electrolyte concentration, and/or the desired target gas detection range can affect the selection of the available area of the separator 120 at the opening 208.

In use, the sensor 100 can detect a target gas concentration of a gas in the environment in which the sensor 100 is disposed. Referring to FIG. 1 and FIG. 2, the gas in the environment around the sensor 100 can enter the housing through an inlet opening 140 so that the target gas can be received within the housing. As described herein, the housing can comprise the counter electrode 111, the reference electrode 113, and the sensing electrode 115. The target gas can contact the separator 120 retaining the electrolyte. The separator 120 with the electrolyte retained therein forms the ionically conductive pathway between each of the electrodes 111, 113, 115, which can be disposed in a planar alignment. In an oxygen sensor, a potentiostatic circuit can be used to maintain a potential of the sensing electrode 115 lower than the reference electrode 113, and as a result, the target gas may begin to be reduced at the sensing electrode 115 while water is oxidized at the counter electrode 111. The target gas can thus be consumed at the sensing electrode 115 and regenerated at the counter electrode 111. Alternatively, in another electrochemical sensor, a potentiostatic circuit may maintain a potential of the sensing electrode 115 higher than the reference electrode 113. The target gas generated at the counter electrode 111 can pass through a diffusional barrier and pass out of the sensor 100 through an exhaust opening 142. A target gas concentration gradient can then be formed in the electrolyte in the separator 120 between the counter electrode 111 and the sensing electrode 115. A current can be developed based on the reaction of the target gas and water at the sensing electrode 115 and the counter electrode 111, which may allow the target gas concentration in the gas contacting the separator 120 to be determined.

During the detection process, the target gas concentration in the electrolyte at or near the sensing electrode 115 can be limited to less than a threshold amount. In general, the target gas concentration in the electrolyte in the separator 120 can be limited to less than a saturation concentration at a predetermined temperature, and in some embodiments, the target gas concentration in the electrolyte in the separator 120 can be limited to less than a percentage of a saturation concentration at a predetermined temperature. In an embodiment the length of the separator 120 and the distance between the counter electrode 111 and the sensing electrode 115 can be selected so that the target gas concentration along the target gas concentration gradient is below the threshold at or near the sensing electrode 115. For example, the target gas concentration along the target gas gradient may be below the saturation concentration in the electrolyte at a predetermined temperature, or below a percentage of a saturation concentration at the predetermined temperature, within about 0.5 mm, within about 1 mm, within about 2 mm, within about 4 mm, or within about 5 mm of the sensing electrode 115.

In some embodiments, the sensing electrode 115 can be disposed within the chamber 206 formed within the housing. The separator 120 can extend into the chamber 206 to provide contact between the electrolyte in the separator 120 and the sensing electrode 115. The separator 120 can be positioned within the chamber 206 and the opening 208 to prevent or limit any gas/electrolyte contact within chamber 206. Controlling how gas moves within the sensor 100 may rely on the fact that gas diffusion through the gas phase is orders of magnitude faster than gas diffusion through liquid. Therefore, while a wetted separator is a very effective barrier to gas diffusion, even a small void or aperture can immediately create a relatively facile gas path. Thus, the separator must completely fill the opening 208 in the barrier to provide the required control. In some embodiments, some amount of gas/electrolyte contact may occur within the chamber 206, but the gas may not be able to be exchanged with a gas outside of the chamber 206, thereby limiting the potential for the formation of a high-target gas concentration gas contacting the electrolyte in the separator 120 near to the sensing electrode 115. The use of the chamber 206 may limit the rate at which the target gas can diffuse to the sensing electrode 115 during the detection process and thereby limit the target gas concentration along the target gas gradient near the sensing electrode 115 to less than the threshold amount.

In some embodiments, limiting the target gas concentration in the electrolyte can include limiting the diffusional flux of target gas through the electrolyte in the separator 120 to less than a rate of target gas oxidation and/or reduction at the sensing electrode 115. In some embodiments, the diffusional flux may be controlled to be lower than the lowest detection limit required of the sensor. The choice of the geometry of the separator 120, the geometry of the chamber 206, the use of one or more breather slots, and/or the relative positioning of the electrodes may all be used to limit the diffusion of target gas in the electrolyte to and/or from the sensing electrode 115.

Figure 3:
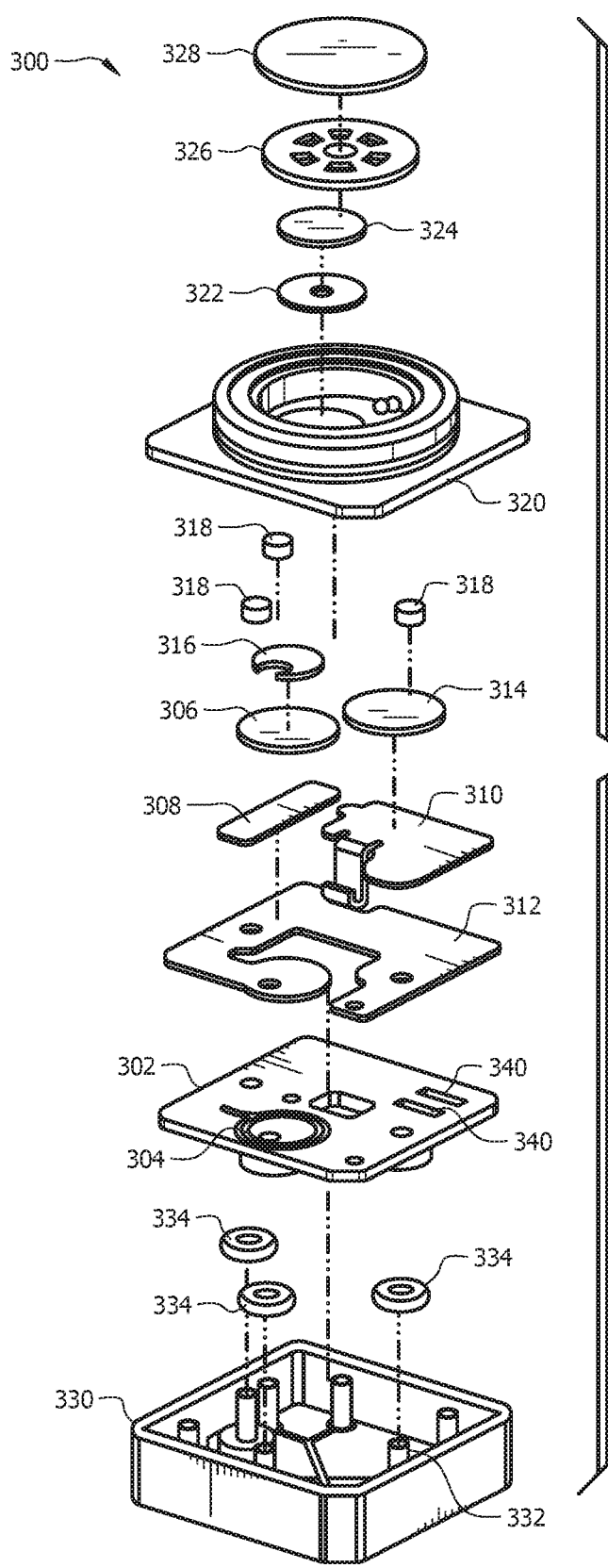
FIG. 3 illustrates an exploded view of an electrochemical gas sensor according to an embodiment.

In the sensor 300 shown in FIG. 3, the sensor 300 may comprise a body 330, a support table 302, one or more O-rings 334 located below the support table 302, a shaped separator 312, a reference electrode 308, a counter electrode 310, and a sensing electrode 306. The sensor 300 may also comprise a vent membrane 314, a sensing electrode diffuser 316, and one or more contact pressure pads 318 operable to apply pressure to the one or more electrodes 306, 308, 310. The sensor 300 may also comprise a top cap 320 with a sealing ring, an adhesive ring 322, a condensation blocker 324, a dust membrane 328 and dust membrane support 326. As shown in the sensor 300, an injection molded thermoplastic elastomer (TPE) (or similar soft material) can be molded to positions on one or more surfaces of the sensor 300. For example, TPE can be molded to one or more surfaces of the body 330 and/or support table 302, where the TPE can aid in creating a seal at different material interfaces. This may prevent electrolyte leaking out of the sensor at the TPE to plastic interfaces and the TPE to electrode material interfaces, and may prevent the electrolyte from contacting corrodible parts, such as the contact pins 332. The compliant nature of the TPE can also take up voids around the sensing electrode 306 further reducing the opportunity of having small air pockets migrating to the sensing electrode 306 and/or reference electrode 308, potentially creating signal instability and/or false alarms. The molded TPE may prevent gases (e.g., $O_2$ on the sensing electrode 306, other cross sensitive gases on the reference electrode 308, etc.) from entering the sensor 300 via the TPE to plastic interface and reacting on the electrodes 306, 308, 310. As shown in FIG. 3, the support table 302 may comprise a raised ring 304 operable to seal around the sensing electrode 306, when the sensor 300 is assembled. In some embodiments of the sensor 300, the support table 302 may comprise one or more breather slots 340 (described in more detail below).

The sensor 300 may be assembled by over-molding the plastic body component using a suitable material, in this case TPE. One or more applications or components could be used, although for cost reasons, a single over-molded application to create the pin seals, oxygen cross over barrier, and/or reference cross over barrier can be used. The compression of the seals may be in the same direction as the component assembly, in this case the Z direction, to facilitate fault finding, although it is possible to assemble in the Z direction and seal in the X and Y directions. The area of the electrode backing tape that is not covered by catalyst may be compressed with the TPE to remove any voids in this area.

In order to reduce any current loss resulting from internal electrical resistance between the electrodes and the current collectors and/or contact pins, a low contact resistance between the current collector and the electrode surface is useful. Typical contact solutions within gas sensors rely on the compression of porous separator components to physically push the current collector into contact with the electrode material. However, this type of compression can result in over-compression of materials such as the separator that is electrically non-conducting and has a low mechanical strength and poor elasticity. Geometric tolerances of the internal sensor components surrounding the compressed separator, variations in the mechanical properties of the separator under compressive load forces, and the susceptibility of all supporting components to compressive creep affect the compression force used to obtain a low contact resistance. Additionally, throughout the operational lifetime of the sensor, the compressive force applied by the separator material on the current collector can be affected by the mechanical forces resulting from external stresses such as vibration, impact, and thermal cycling. For many sensor designs, the resultant increase in electrical contact resistance can potentially result in various failure modes such as partial/complete loss of sensor output and/or slow speed of response to the target gas.

In order to address potential over-compression issues, the elements of the sensor may be designed to separate the compression requirements for ensuring contact between the electrolyte-retaining materials with the electrodes (e.g., the separator, etc.) and between the electrical contacts by which the electrodes are connected to the external circuit. The separation of the compression regions may allow a solid pin (e.g., a contact pin surface) to contact the electrode, rather than requiring an intermediate connection to a flexible ribbon current connector, which is compatible with compression within a stack.

FIG. 4 illustrates a means of facilitating hard contact points between electrodes and current collectors in electrochemical sensors. The sensor 400 shown in FIG. 4 takes the electrical connection between each electrode 410 and its associated contact pin outside of the electrode stack (defined as the area of layered components wherein each component is in intimate contact with components both above and below it). The sensor 400 can have an alternative electrode geometry (shown in FIG. 5A) that incorporates at least one protruding tab 411 that can be oriented to the point of electrical connection to the pin outside of the electrode stack where a hard plastic or sprung plug 412 can be used to create a low contact resistance under high compressive force without applying the compressive force to the separators 404 within the electrode stack. In an embodiment of the sensor 400, one or more of the separators 404 may comprise a shape matched to the electrode 410 shown in FIG. 5A, where the tab of the separator 404 may be compressed with the tab of the electrodes 410. The electrical contact can be made with the electrode material. When a separator 404 is present, a foil or other contact can extend between the electrode and the separator, where the presence of the separator should not interfere with the electrical contact formed by the compression of the materials. Utilizing a protruding tab 411 has the added benefit that a sensor designer may be able to optimize the electrode stack compression differently than the electrical contact compression to thereby provide for effective electrolyte wicking and retention by the porous separator material(s) and extend the operational humidity and temperature range(s) of the sensor 400.

Figure 6:
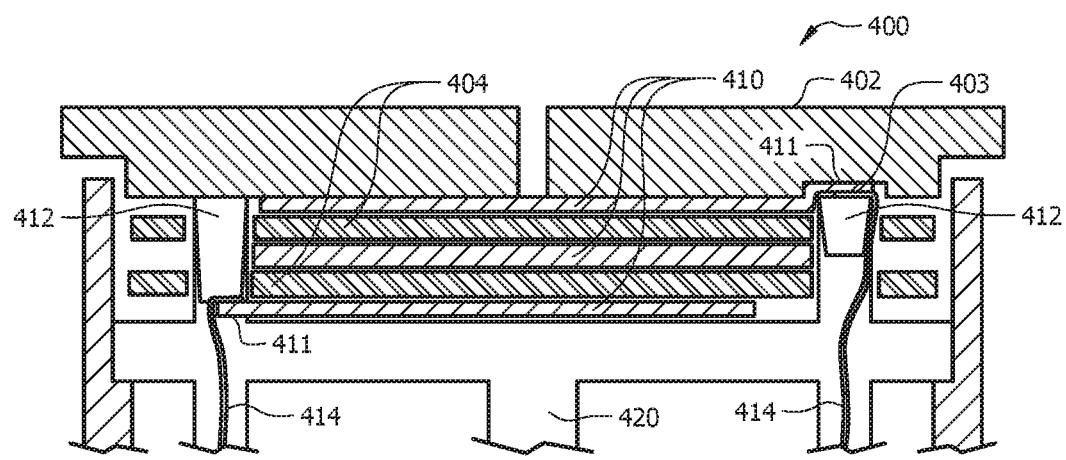
FIG. 6 illustrates another cross-sectional view of an electrochemical gas sensor according to an embodiment.

The sensor 400 may comprise a housing 401 defining an interior space (or reservoir) 430. The sensor 400 may comprise one or more separators 404 (also shown in FIG. 5B), wherein the separators 404 may be shaped to fit around the plugs 412. In an embodiment of the sensor 400, the electrodes 410 may comprise a shape matched to the separator 404 shown in FIG. 5B, where the edges of the electrodes 410 and/or separator 404 may be compressed by the plugs 412. In the sensor 400 shown in FIGS. 4 and 6, a flexible current collector 414 may be electrically coupled to the electrodes and the external contact pins. A portion of the current collector(s) 414 may be held between the tabs 411 of the electrodes 410 and the plugs 412, wherein the plugs 412 create a first compression force on the portion of the current collector 414 and the tab 411. The plugs 412 can comprise a resilient material that provides a biasing force when compressed. The plugs 412 can also be formed from a chemically inert material to avoid corrosion issues within the sensor when contacted by the electrolyte. The electrode stack may be held between the top cap 402 and the table 420. During assembly of the sensor 400, the electrode stack can be placed under a second compression force by the assembly of the top cap 402 and the table 420. The first compression force may be different from the second compression force. In an embodiment of the sensor, the first compression force may be greater than the second compression force. Alternatively, the second compression force may be greater than the first compression force. In FIG. 6, the top cap 402 of the sensor 400 may comprise an indent 403 allowing the tab 411 to extend into the indent 403.

Figure 7:
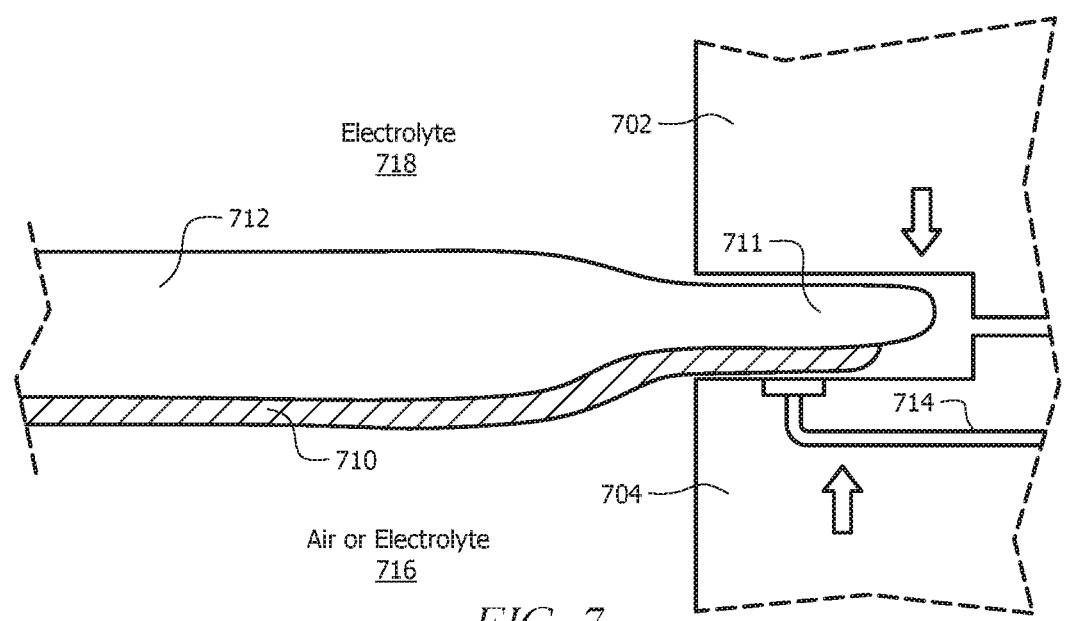
FIG. 7 illustrates the compression of a housing on a portion of an electrode within an electrochemical gas sensor according to an embodiment.

In some aspects, a lead frame can be used to improve contact between a current collector or contact pin and an electrode in an electrochemical gas sensor. This configuration may help to avoid the use of current collectors and improve sealing around the edges of electrodes to prevent gas access via diffusion, bulk flow etc. As shown in FIG. 7, instead of using a wire or ribbon current collector pressed against the sensing electrode, the edges of the electrode 710 and/or the supporting tape (or separator) 712 may be clamped between two or more parts of the housing 702 and 704. The housing 704 may comprise a polymer with a molded-in lead frame 714 so that the lead frame 714 contacts the edge of electrode 710. The housing 702 and 704 may be designed such that the lead frame 714 does not contact the electrolyte 718 but is sealed from it by compression against the electrode 710 and supporting tape 712. Alternatively, exposed parts of lead frame 714 could be plated with a metal which will not adversely interact with the electrolyte, including any of those metals described herein with respect to the contact pins such as gold, platinum, silver, tantalum, niobium, tin, or the like, where the composition may depend on the electrolyte used.

In FIG. 7, the electrode 710 is supported on supporting tape 712. The edge 711 of the electrode 710 and backing tape 712 can be clamped between two parts of housing 702 and 704 which may optionally contain a molded in lead frame 714. The approach may be used with the sensing electrode where regions 718 and 716 can be electrolyte and air respectively, or a reference or counter electrode where regions 718 and 716 may both be electrolyte. Additionally, the approach of clamping the edge 711 may be used with a separator or ionically conducting membrane in place of the supporting tape 712 as a diffusion or bulk flow barrier, in which case the electrode 710 and lead frame 714 may not be required.

Figure 8A:
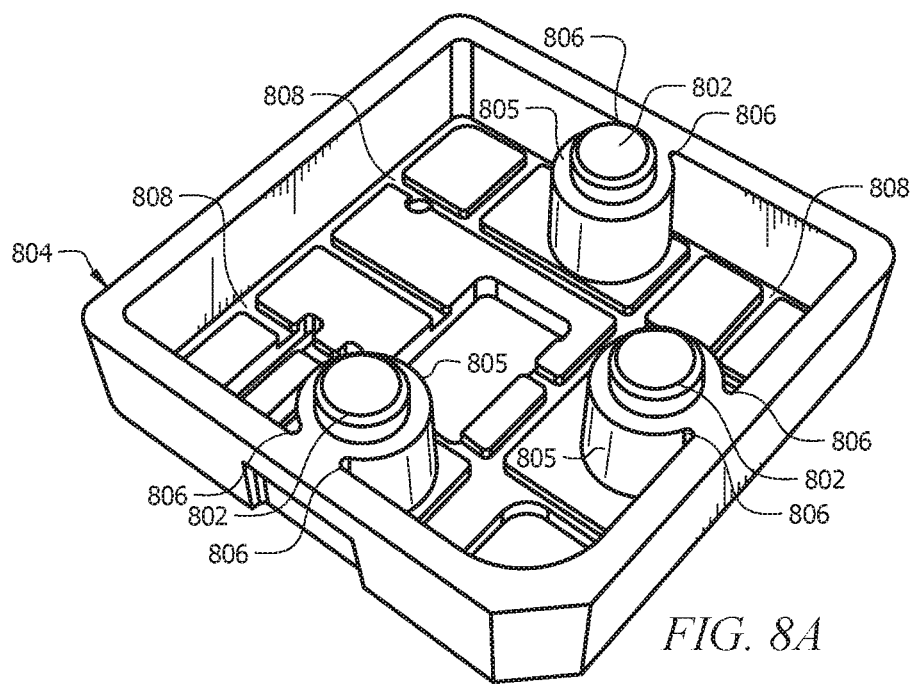
FIG. 8A illustrates a housing for use with an electrochemical gas sensor according to an embodiment.
Figure 8B:
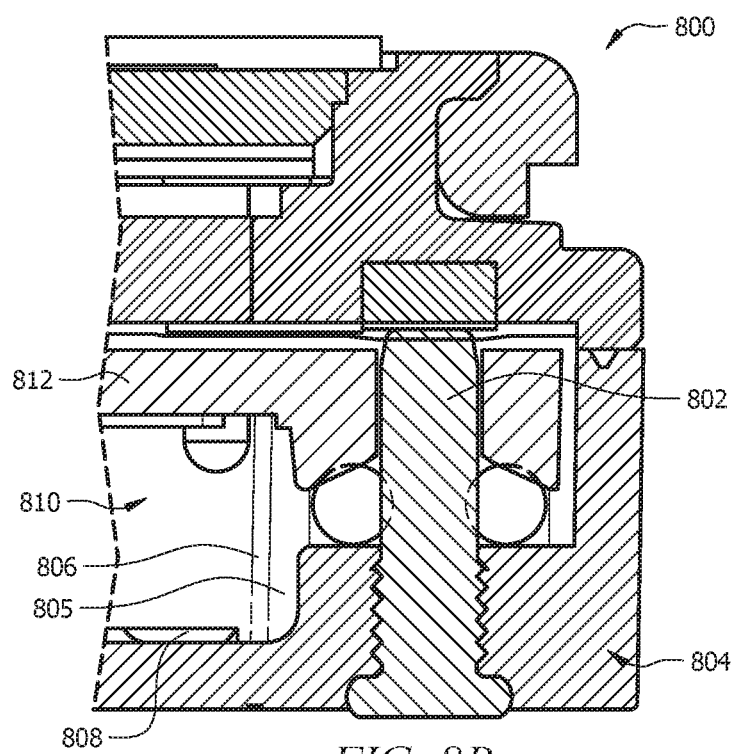
FIG. 8B illustrates a cross-sectional view of the housing of FIG. 8A incorporated into an electrochemical gas sensor according to an embodiment.

As shown in FIGS. 8A-8B, the sensor 800 may use contact pins 802 passing through the sensor body to press directly against the electrode. The required compression can be applied via a compliant pad such as the plugs described herein. As described in more detail herein, the compression of the contact pins 802 with the electrodes may be separate from the compression applied to the electrolyte containing wicking elements (e.g., one or more separators, etc.) in the sensor. Sealing of the contact pins 802 against electrolyte leakage may be achieved by a variety of methods. For example, the sealing may be achieved by using epoxy potting at the base of the contact pins. The sealing may alternatively or additionally use a long molded-in section with barb or side extension structures to increase electrolyte tracking path-length between the contact pin surface and the wall of the housing. The overall path-length used to prevent leaks can increase the thickness of the wall section as the path-length increases, wherein the path-length may be limited in some instances by the available thickness of the wall section. The seal may also use one or more O-ring seals disposed in a suitable recess in the contact pin and/or body. In some designs, over-molded O-ring seals can be used instead of separate seal components disposed in any recesses.

The material of the contact pins 802 in any of the configurations described in this entire disclosure can be chosen to protect the pins from the electrolyte. For example, the connector pins can be formed from an electrically conductive and corrosive material (brass, nickel, copper, or the like) which may be plated or coated to reduce degradation due to the contact with the electrolyte. For example, the coating may comprise one of gold, tungsten, niobium, tantalum, platinum, or any alloy or combination thereof. Alternatively, the material of the connector pins may be non-corrosive. Exemplary materials include gold, tungsten, niobium, tantalum, platinum, or any alloy or combination thereof.

While the above sensor is described in the context of an oxygen sensor, similar concepts and practices could be used in a variety of electrochemical sensors.

In some aspects, wicking structures can be used with the sensor to improve the sensor performance. Electrochemical systems employ a variety of electrolytes having a range of physical properties. Typically, successful practical designs for small, low cost, low power sensors may rely on liquid electrolytes such as sulfuric acid. Despite the challenges involved in retaining such aggressive materials within housings and dealing with material compatibility issues, liquid electrolytes still may offer improved environmental performance, which is a key driver for devices which must operate in a wide range of environmental conditions, including a large range in temperatures and humidity.

Proper transport of the electrolyte within the sensor allows the separator, and more particularly the desired portions of the separator, to remain wetted to maintain proper operation of the sensors. In general, the electrochemical reactions occur at the three-phase interface between the catalysts, gas, and electrolyte. For systems utilizing liquid electrolytes, the electrolyte must be transported from a reservoir to the areas adjacent to the electrodes to form the three-phase interface. If the electrolyte is not adequately transported to the appropriate locations within the separator, then a sensor placed under environmental stress may fail due to an inadequate formation of the three-phase interface. For example, the separator may dry out at or near an electrode, resulting in an inadequate performance of the sensor.

In order to improve the electrolyte transport within the sensor, channels can be used within the sensor that preferentially move the liquid to the perimeter of the reservoir where the electrolyte can be transported into contact with the separator and/or a specially formed and treated separator, which is differentially compressed by mating features on the sensor casing parts.

The channels can be used in conjunction with wicking features to transport the electrolyte to the internal components in order for them to function correctly. For example, gas diffusion electrodes need to be partially wetted and provided with ionic connection between other electrodes in order to produce a functional electrochemical cell and separators require the electrolyte to form barriers to internal gas flow. Additionally, the ratio between the total available internal free space and the electrolyte volume contributes to (and may define) the environmental "window" (or time to failure) under specified operational environmental conditions of temperature and humidity, and so it is desirable to utilize a component that fills as small a volume as possible in order to improve the environmental window for the product.

In an embodiment of a sensor, the walls, floor, and ceiling of the reservoir may be utilized to create surface "buttresses" provided with channels, where the dimensions of the channels are chosen to promote electrolyte transport. In some aspects, larger channels can be used to direct the fluid flow to certain areas within the reservoir where the electrolyte can contact wicking features. The dimensions of the wicking features may be small enough to create a capillary effect, allowing the liquid electrolyte to be transported by the channels to the separator. The one or more molded or machined channels located within the reservoir may be used to transport the free electrolyte towards a separator material, which has a pore size volume distribution under the local conditions of compression to produce a differential capillary attraction which draws the electrolyte from the mechanical wicking channel into the separator to thereby enable both the separator and contacting gas diffusion electrodes to function correctly. By using the appropriate combination of larger channels to direct the electrolyte and wicking features to transport the electrolyte from the reservoir to the separator, the location of the wetting of the separator can be controlled to some degree. For example, the wicking features may be aligned to provide the electrolyte at or near one or more of the electrodes.

As shown in FIG. 8A, the base of the housing 804 may comprise one or more pins 802 (described above). The pins 802 may fit into bosses 805, wherein the bosses 805 may comprise narrow corners 806 at the attachment point between the bosses 805 and the housing 804. These corners 806 may have features comprising at least three-sided channels with dimensions that are suitable for wicking the electrolyte located within the housing 804 upward toward the pins 802, wherein the electrolyte may be directed into the separator at or near the contact point with the pins 802. Additionally, the housing may comprise one or more wicking channels 808 located throughout the base of the housing 804, wherein the wicking channels 808 may be operable to direct electrolyte flow, particularly when the level of electrolyte within the reservoir of the housing 804 is low. In other words, the channels 808 may cause the electrolyte to flow and/or be directed by capillary forces to the corners 806 of the bosses 805, where the electrolyte may then be directed upward, via capillary forces at the corners 806, into the separator.

In some embodiments, one or more surfaces of the channels 808 and/or the capillaries can be surface treated to provide a suitably attractive finish to aid in directing the fluid flow. For example, when the electrolyte comprises an aqueous fluid, the surfaces can be treated to be hydrophilic to attract the electrolyte and aid in transporting the electrolyte to the desired area in the base and into the separator. Various surface treatments such as a plasma treatment can be used to modify the surface. In some embodiments, portions of the base can be treated to be hydrophobic to direct the electrolyte to the desired wicking areas, which can then be suitably hydrophilic. The selection of material for the formation of the base may also be based on the type of electrolyte to take into account the desire to direct the flow of the fluid into the desired area. For non-aqueous electrolytes, the surface treatment can be selected to produce the desired attractive or repulsive forces to help direct the electrolyte to the wicking features.

FIG. 8B shows a cross-sectional view of the assembled sensor 800, where the channels 808 may direct electrolyte flow within the reservoir 810 toward the corner 806 of the boss 805. Then, the corner 806 may direct electrolyte flow into the separator 812. The channels 808 may be particularly effective in areas located furthest from the bosses 805 along relatively large, flat surfaces along the base of the housing 804.

In some sensors, the channels 808 may comprise a width of approximately 250 micrometers (μm). In some sensors, the channels 808 may comprise a width of approximately 300 μm. In some sensors, the channels 808 may comprise a width between approximately 200 μm and 400 μm. In some sensors, the channels 808 may comprise a width between approximately 100 μm and 500 μm. In some sensors, the channels 808 may comprise a width less than approximately 500 μm. In some sensors, the channels 808 may comprise a depth of approximately 500 μm. In some sensors, the channels 808 may comprise a depth less than approximately 600 μm. In some embodiments, the channels 808 can be significantly larger (e.g., to server as bulk flow channels) and only the wicking features 806 at or around the bosses 805 may comprise small dimensions.

The use of the channels, as described above, may ensure that even when there is relatively little electrolyte within the sensor, the electrolyte is localized at or near wicking features and then moved (via the channels) to the points where the buttresses intersect the separator. The separator may then absorb the liquid, thereby ensuring that the electrodes are preferentially wetted. This functionality is assisted by the use of differential compression and/or selective control of the degree of hydrophobicity of different regions of the separator. The buttresses may access the separator at a number of cut-outs around the perimeter of the support table which align with the capillary buttresses in the reservoir walls below.

When the electrolyte volume is high (for example after extended periods spent in high humidity environments), there is likely to be free electrolyte (i.e. not localized within the separator or the buttress slots) within the reservoir. In this case, depending upon the orientation of the sensor, the electrolyte may additionally contact the separator through the free space where the counter electrode breather tab (as described in more detail herein) can pass through the support table and/or through the breather slots in the support table under the counter electrode.

The use of channels within the reservoir may reduce the part count necessary to produce the internal capillary forces required for directional flow of an aqueous electrolyte. Introducing sharp geometric edges, either by insert molding or machining, may create high energy surfaces that preferentially wet and produce desirable differential surface energies that effectively retain the electrolyte within the mechanical wicking "channel". The effectiveness and wettability of a wicking channel (generated by higher surface energy) seems from practical experimentation to be superior for channels previously wetted by acid and/or plasma conditioning.

Figure 9A:
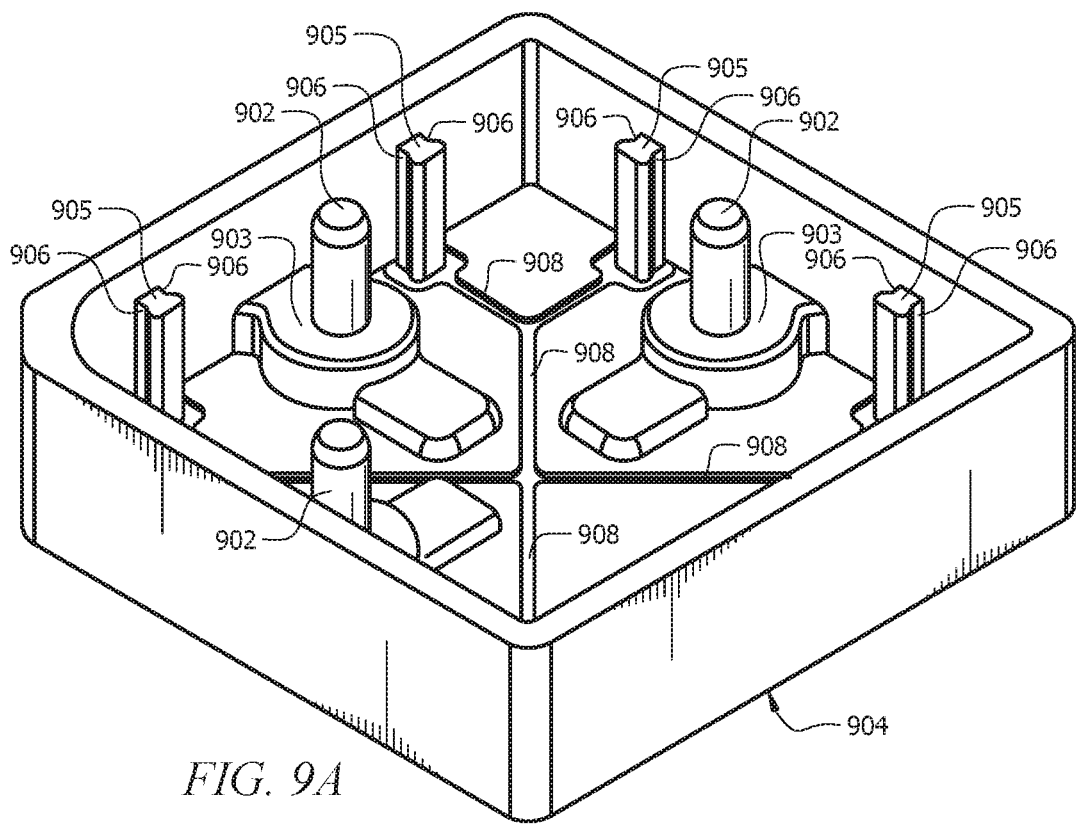
FIG. 9A illustrates a housing for use in an electrochemical sensor according to an embodiment.

Referring now to FIG. 9A the mechanical wicking features in the housing 904 comprise a mixture of channels 908 and vertical ridges (or buttresses) 905 whose profile includes narrow portions 906 shaped to promote the required capillary motion of electrolyte. In the housing 904 shown in FIG. 9A the connection pins 902 are encased in the housing 904 along only a portion of their length. This may provide manufacturing advantages (in terms of pin retention in the molding tool used to form the housing), and may provide a flat top to the boss 903 where an O ring 922 (shown in FIG. 9C) can be located as an electrolyte seal.

Figure 9B:
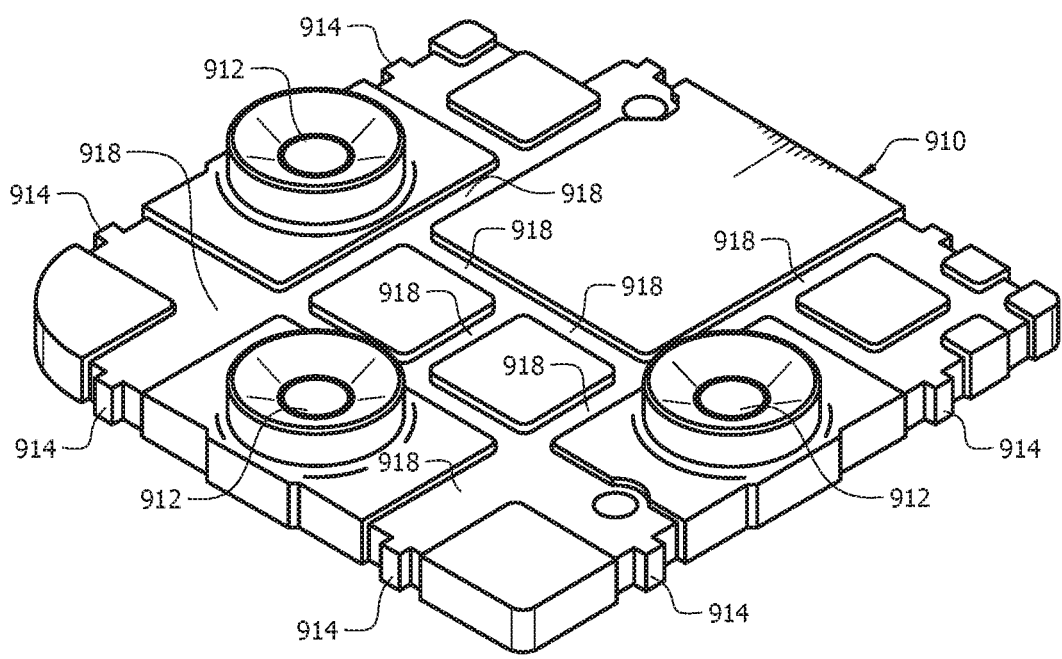
FIG. 9B illustrates a table for use in an electrochemical sensor according to an embodiment.

As the pin bosses 903 no longer reach the table, additional upstanding buttresses 905 have been added to transport electrolyte up the side walls ('up' refers to the 'normal' sensor orientation but is understood to have little meaning in practical applications where the device can rest in any orientation). Referring now to FIG. 9B, the table 910 may comprise saucer-shape connection points 912 operable to fit over the pins 902 held within the housing 904, wherein an O-ring may fit between the bosses 903 and the connection points 912. Additionally, the table 910 may comprise indentations 914 around the edge of the table, where the buttresses 905 may mate with these indentations 914 and therefore allow contact with the separator (wherein the table 910 may be located between the buttresses 905 and the separator. The table 910 may also comprise wicking channels 918 operable to direct electrolyte toward the indentations 914.

Figure 9C:
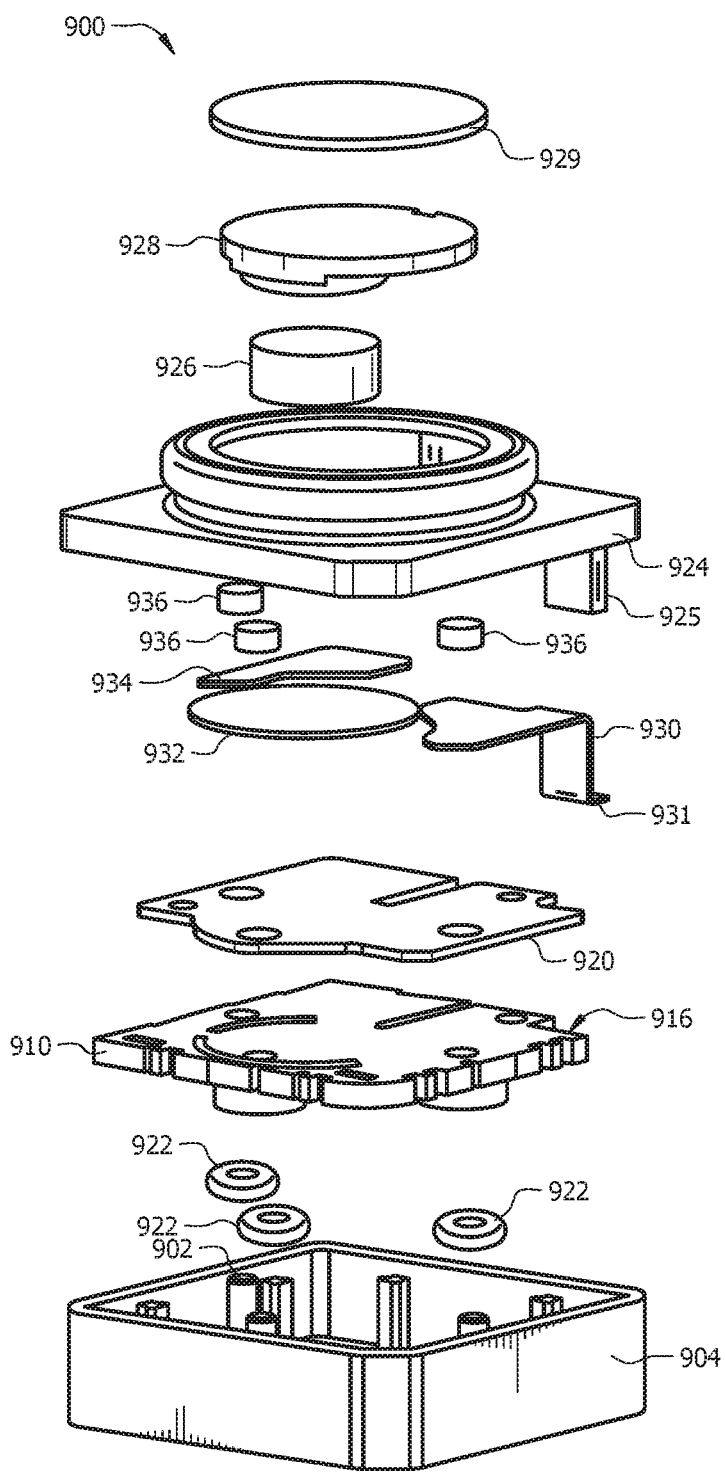
FIG. 9C illustrates an exploded view of an electrochemical gas sensor according to an embodiment.

Referring now to FIG. 9C, an exploded view of the electrochemical gas sensor 900 is shown. As described above, O-rings 922 may fit over the pins 902 within the housing 904, and the table 910 may fit over the O-rings 922. The O-rings 922 may be compressed by the saucer-shaped features on the underside of the table 910. The separator 920 may be located against a surface of the table 910, wherein electrolyte may be wicked through the table 910 into the separator 920. The separator 920 may be in contact with a plurality of electrodes 930, 932, and 934. A top cap 924 may fit over the other elements onto the top of the housing 904, wherein compression plugs 936 may be located over the contact points between the pins 902 and the electrodes (where the pins 902 extend through the table 910 and the separator 920). The top cap 924 may also comprise a filter 926, a restrictor 928 and/or a dust cover 929 located over the inlet/outlet of the sensor 900.

The sensor table 910 may comprise a rectangular cutout 916 to allow a protrusion feature 925 of the top cap 924, as well as a breather tab 931 to pass through the table 910 into the housing 904 (as described in more detail below).

Figure 9D:
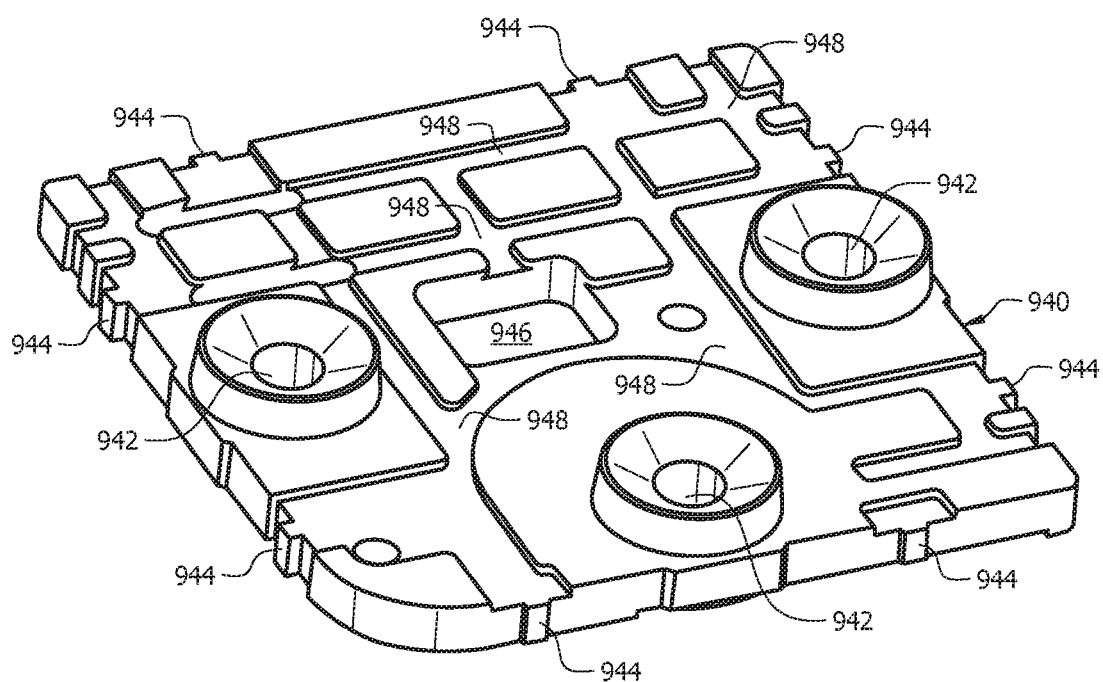
FIG. 9D illustrates a table for use in an electrochemical gas sensor according to an embodiment.

FIG. 9D illustrates another embodiment of a table 940 comprising saucer-shaped connection points 942, indentations 944, and wicking channels 948. The pattern of the wicking channels 948 may vary depending on the application and use of the sensor. Additionally, the table 940 may comprise a cut-out 946 located somewhere within the table 940.

Figure 9G:
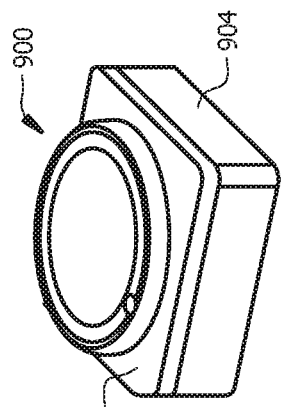
FIGS. 9E-9G illustrate steps of assembling an electrochemical gas sensor according to an embodiment.
Figure 9F:
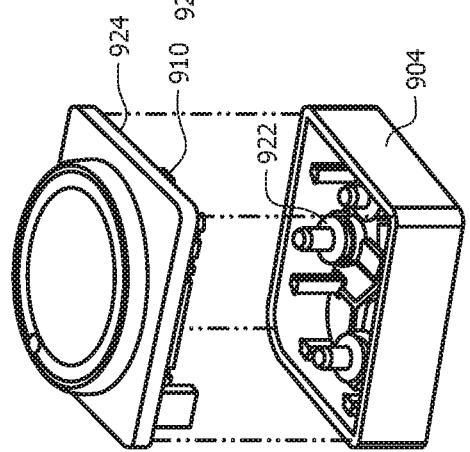
Figure 9E:
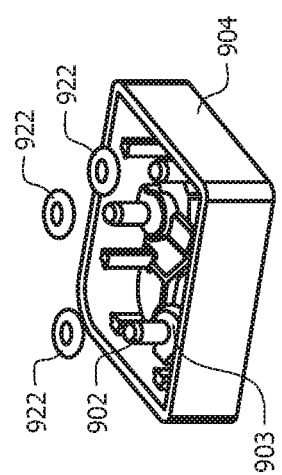

FIGS. 9E-9G illustrates an assembly of the sensor 900. The O-rings 922 may be installed over the pins 902 of the housing 904. The top cap 924 may be assembled with the table 910 (and separator) and installed onto the housing 904, wherein the table 910 contacts the O-rings 922. FIG. 9G shows the assembled sensor 900.

The sensors as described herein can use a suitable electrolyte to provide the ionic conduction of charge necessary for correct electrochemical operation. Typically, sensor designs have electrode components nominally perpendicular to a common axis, referred to hereafter as a "stacked" design. Such stacked designs can include a plurality of separators between the stacked electrodes to electrically isolate the electrodes while maintaining the electrolyte in contact with the electrodes.

Typical separators may be formed from fiber sheet material that is cut or punched into a simple geometric shape for ease of manufacture. When filled with an electrolyte, the separator may bias the effective cross sectional areas of the interfacial phases towards solid/liquid/solid (e.g., catalyst/electrolyte/catalyst) interfaces rather than the liquid/gas (e.g., electrolyte/internal "air" reservoir) interfaces at the edges of these stacked components.

In an embodiment of a sensor, the sensor may comprise a shaped separator containing electrolyte that is in intimate contact with two or three electrodes orientated nominally in a common plane, referred to hereafter as a "planar" design, to provide the ionic connectivity required for operation of an electrochemical sensor. A planar arrangement of electrodes offers a practical solution to the primary issue of separately improving the compression required for fluid transport and electrical connectivity, as described in more detail herein.

Lateral separation of electrodes allows separation and simplified, more accurate control of the compression applied to fluid transport and connection aspects. For example, one separator overlaying an electrode (which can be connected electrically via a completely different part of the structure) has a more controllably defined compressibility than a conventional stacked design having 3 electrodes, 3 or more separators, insulators, and current collectors, all of which can have competing compression needs. In addition to better fundamental control, the planar arrangement also allows lateral variation of compression across these well-defined structures which can be beneficial (e.g., in promoting and/or selectively controlling electrolyte transport). This can be achieved by hard features on the sensor casing and/or table to increase/decrease pressure on chosen areas of absorbents. For example, a distance or gap between the sensor casing and table can vary laterally to thereby variably compress the separator across the sensor. Another benefit of planar designs is that the overall volume of separator material required to ensure the full electrode areas remain in contact with electrolyte is reduced, even without shrinking the size of the electrodes themselves.

A planar electrode arrangement can use a planar separator arrangement. A planar separator allows for the use of a single shaped component rather than separate components for each separator, thereby allowing for simplifications in assembly and improvements in reliability. Planar separators can suffer from electrolyte transport issues, which may result in portions of the separator having an insufficient supply of electrolyte, even while other portions may be saturated with the electrolyte. This may be true, for example, when a gas is evolved from an electrode, which can result in the evaporation of a portion of the electrolyte. As a result, electrolyte transport within the planar separator may need to be controlled during operation.

The variance in geometry of the shaped planar separator may also allow the ionic resistance between the electrode pairs to be selectively modified during the design and construction of the sensor. For example, a thin strip of wetted separator may connect an "isolated" (e.g., not located directly on a flow path between the sensing and counter electrode) reference electrode to the potentiostatic controlled sensing electrode, providing similar functionality to that of a "Luggin" capillary.

Forming the shaped separator may comprise laser cutting of a sheet material, which may allow for complex and accurate parts to be manufactured, thereby reducing geometric tolerances in the X-Y plane and reducing variations in the stack compression due to the localized glass density, pore volume, and tortuosity. By reducing the number of separator layers used for a typical stacked sensor design and the large cross sectional areas of the separator that are used to provide a sufficiently large area of contact between opposing separators, the "environmental window" (as described above) of operation can be increased as a result of needing less electrolyte to wet the smaller volume of separator material.

Further modification of the glass density, and thereby the porosity of the separator, can be made in the Z axis by local compression of the separator between opposing faces of the sensor enclosure, care being required not to damage the fibers (e.g., glass fibers, polymer fibers, etc.) of the separator. The separator might be configured to improve the electrochemical performance of the electrochemical sensor, for example, by reducing any "polarization" effects associated with the local proton concentration in the electrolyte which can lead to a dramatic disturbance in the electrochemistry occurring at the three electrodes.

Additional benefits to a planar electrode and separator configuration can include the effective formation of a feature known in the industry as a "partition" between the reference and sensing electrodes. According to standard fluid dynamics for a non-compressible liquid in a tube (e.g. the Hagen-Poiseuille equation states that the volumetric flow rate is inversely proportional the length of the tube, analogous to the length of the porous wetted separator in this case) the increased resistance to electrolyte flow will effectively make the sensor more tolerant to internal pressure differences resulting from environmental transients of pressure and/or temperature that might generate a current "spike" or "glitch," as described in more detail herein. However, any increase in the resistance to electrolyte flow may also reduce the ability for the electrolyte to flow and wet various areas of the separator.

Figure 10:
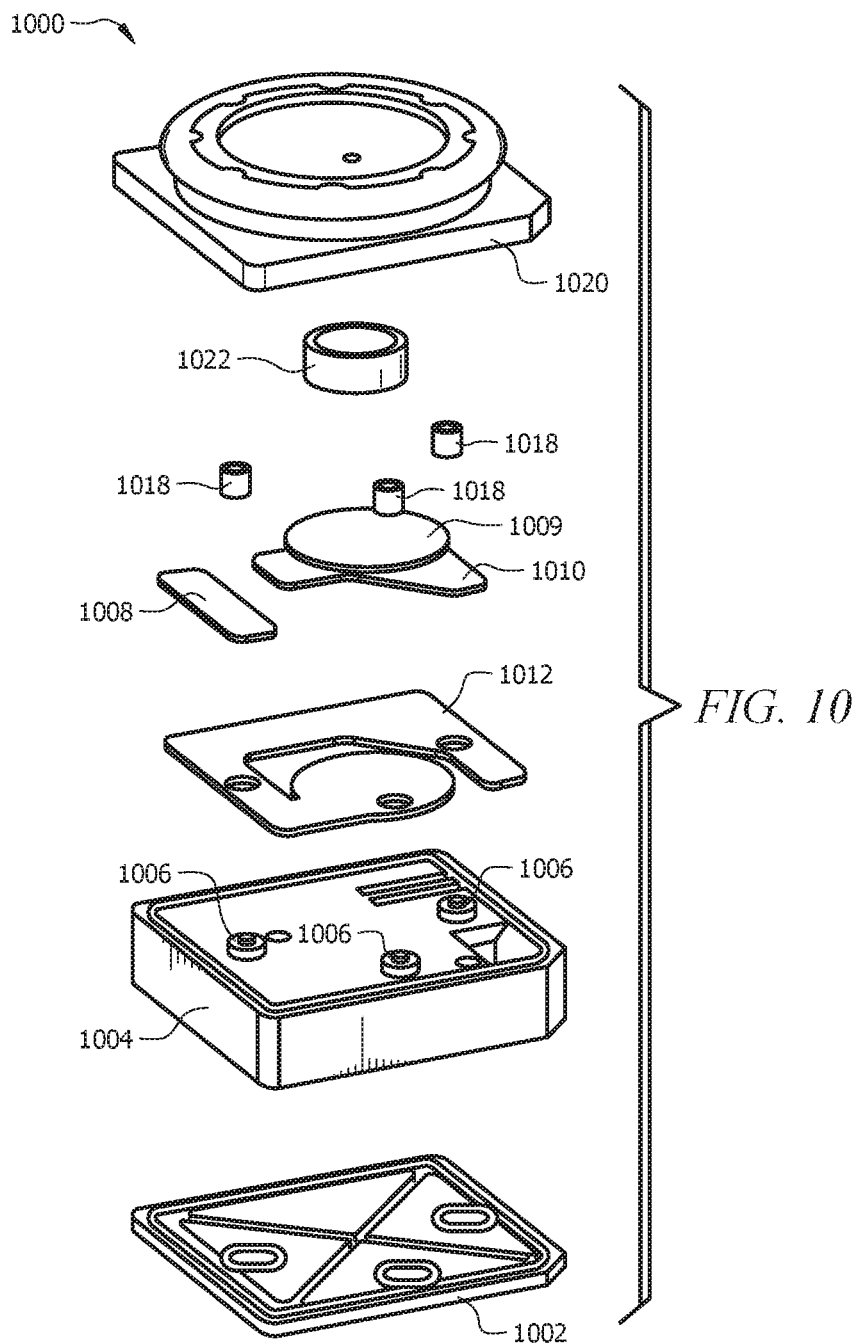
FIG. 10 illustrates an exploded view of an electrochemical gas sensor according to an embodiment.

FIG. 10 illustrates an exploded view of a sensor 1000, wherein the sensor 1000 comprises a body 1004 and base 1002. The body 1004 may comprise contact pins 1006 operable to pass through a separator 1012 (which may be a shaped separator) to contact electrodes (counter electrode 1010, reference electrode 1008, and sensing electrode 1009). The sensor 1000 may also comprise pressure pads 1018 operable to apply pressure to the electrodes 1008, 1009, 1010 and the contact pins 1006 to ensure a low resistance electrically coupling between the contact pins 1006 and the electrodes 1008, 1009, 1010. As noted herein, current collectors could also be used in various configurations to electrically couple the contact pins 1006 with the electrodes 1008, 1009, 1010. The sensor 1000 may also comprise a top cap 1020 operable to seal with the body 1004, as well as a carbon cloth 1022, or other filter(s) or membranes.

The shaped separator 1012 can be used to create an ionic path with the width of the separator 1012 controlling the ionic resistance between each electrode. Also, the separator 1012 can create electrical isolation between the electrodes when required. The separator 1012 also provides water management by compression of specific areas of the separator 1012, or by thinning the separator 1012 with a laser, both of which can be used to control the local density and porosity of the separator 1012. The separator 1012 may create a wetted barrier to prevent gases (e.g., gases comprising oxygen) from directly contacting the sensing electrode 1009. By using the shaped separator 1012, the force (or pressure) required to create an electrical contact with the electrodes may be separately controlled from the compression force required for the desired level of capillary action through the separator 1012.

Controlling the density and/or compression of the separator 1012 along its length may allow for one or more gradients to be formed within the separator 1012 material, where the flow of the electrolyte through the separator 1012 may be controlled by the gradients. The separator 1012 may be formed of a fiber material (such as glass fibers) where the fibers may have a consistent size or diameter. Therefore, when portions of the fiber material are removed, and the separator is compressed within the assembled sensor, different sized voids may be created between the glass fibers. This may create differences in capillary attraction within the separator 1012 and therefore directionality for the electrolyte to flow within the separator 1012. The voids may also create localized reservoirs for retention of the electrolyte. The retained electrolyte can then flow into an area as needed in the event of electrolyte loss, for example as a result of drying out at one or more locations (e.g., at or near an electrode).

An application of this technique may allow for localization of electrolyte around one or more of the electrodes. For example, water exchange between the interior and exterior of the sensor may occur more rapidly at certain locations within the sensor (such as the counter electrode and/or the sensing electrode). By altering the density and compression of the separator, the flow of the electrolyte within the separator may be directed toward these locations where water is lost, increasing the performance of the sensor. Additionally, the flow of the electrolyte within the separator may be controlled for sensors used in extreme dry or wet conditions, depending on the problems created within the sensor by these conditions.

Figure 11:
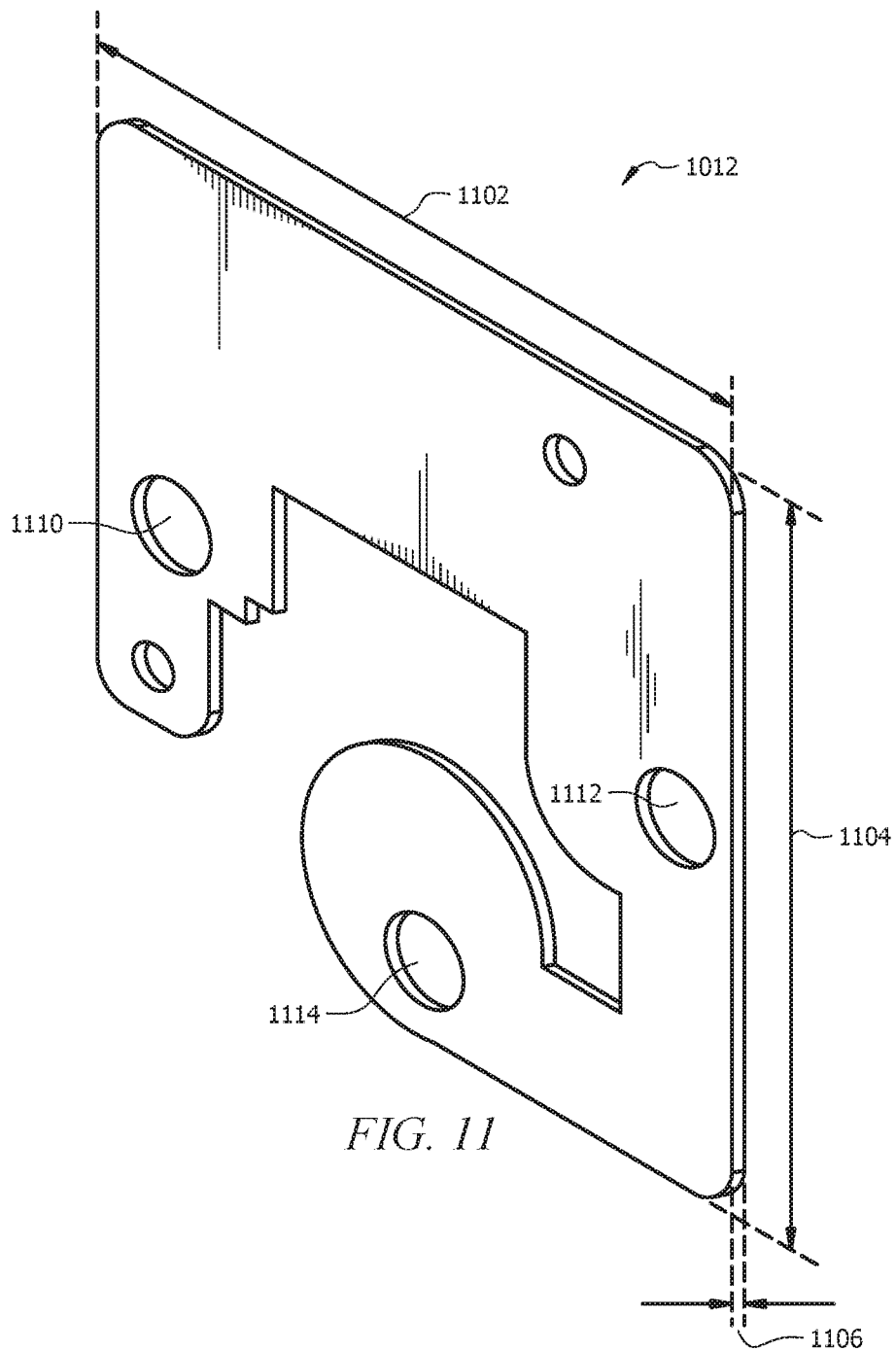
FIG. 11 illustrates a planar separator for use in an electrochemical gas sensor according to an embodiment.

FIG. 11 shows the shaped separator 1012, which may be defined as "planar." The separator 1012 may be formed from any of the materials described herein as being used to form the separator 1012. The planar shaped separator 1012 may comprise a width 1102, a length 1104, and a thickness 1106. The planar shaped separator 1012 may also comprise elements (contact points, cut-outs, thinned portions, shaped portions) which may vary and may be adjusted based on the application and use of the separator 1012.

In an embodiment of a planar separator 1012, the ratio of the length 1104 and/or width 1102 to the overall thickness 1106 may be at least 20/1. In an embodiment of a planar separator 1012, the ratio of the length 1104 and/or width 1102 to the overall thickness 1106 may be at least 40/1. In an embodiment of a planar separator 1012, the ratio of the length 1104 and/or width 1102 to the overall thickness 1106 may be approximately 70/1.

In an embodiment of a planar separator 1012, the thickness 1106 may be less than approximately 10% of the width 1102 and/or length 1104. In an embodiment of a planar separator 1012, the thickness 1106 may be less than approximately 2% of the width 1102 and/or length 1104. In an embodiment of a planar separator 1012, the thickness 1106 may be approximately 1.5% of the width 1102 and/or length 1104.

In some cases, the separator 1012 may have a thickness 1106 of less than approximately 0.5 millimeters (mm). In some cases, the separator 1012 may have a thickness 1106 of approximately 0.25 mm. In some cases, the separator 1012 may have a width 1102 of at least approximately 5 mm. In some cases, the separator 1012 may have a width 1102 of at least approximately 10 mm. In some cases, the separator 1012 may have a width 1102 of approximately 17.5 mm. In some cases, the separator 1012 may have a length 1104 of at least approximately 5 mm. In some cases, the separator 1012 may have a length 1104 of at least approximately 10 mm. In some cases, the separator 1012 may have a length 1104 of approximately 17 mm.

The separator 1012 may comprise openings (or contacts) 1110, 1112, and 1114 for providing contact points between the electrodes and the pins. The distance along the separator 1012 between the contacts 1110 and 1112 may be at least approximately 10 mm (between counter electrode 1010 and reference electrode 1008). In some cases, the distance along the separator 1012 between the contacts 1110 and 1112 may be at least approximately 15 mm.

The distance along the shaped separator 1012 between the contacts 1112 and 1114 may be at least approximately 10 mm (between reference electrode 1008 and sensing electrode 1009). In some cases, the distance along the separator 1012 between the contacts 1112 and 1114 may be at least approximately 10 mm.

The distance along the separator 1012 between contacts 1110 and 1112 may be greater than the length along the separator 1012 between contacts 1112 and 1114. The width of the separator 1012 between the contacts 1110 and 1112 may be greater than the width of the separator 1012 between the contacts 1112 and 1114. In other words, the overall area of the separator 1012 between the contacts 1110 and 1112 may be greater than the overall area of the separator 1012 between the contacts 1112 and 1114.

Figure 12A:
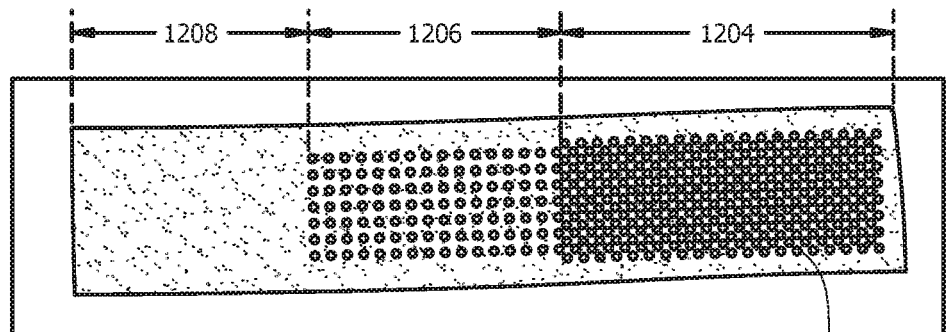
FIGS. 12A-12C illustrate different methods of removing material from a planar separator according to an embodiment.
Figure 12B:
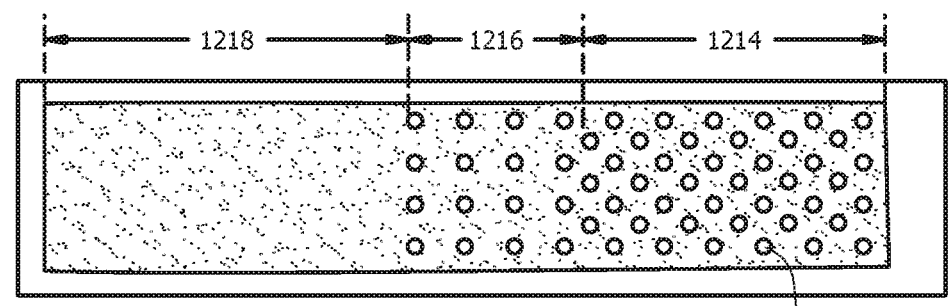
Figure 12C:
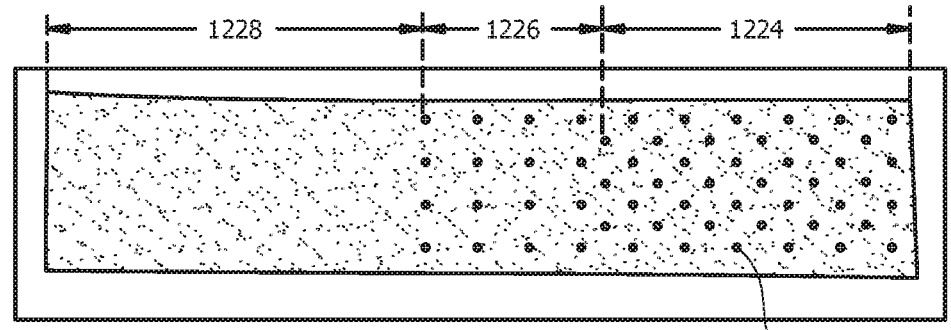

As shown in FIGS. 12A-12C, when the separator material is placed and retained between parallel surfaces, a distribution of "pores" may be created throughout the separator material, which can be utilized to both retain and wick (by capillary attraction) aqueous electrolytes. One method of modifying the local porosity of these materials involves the inclusion of local geometric features. Additionally, by employing a laser cutting process to selectively ablate (or remove) glass fiber material from the separator, the local glass density can be reduced.

A typical "reservoir" design would involve an internal volume that is free of glass fiber material (maximum volume with minimum electrolyte retention) that contains "free" electrolyte that might contact the compressed separator material (i.e. a step change to uniform porosity) and thereby be wicked away from the reservoir by capillary attraction. A separator may also comprise additional separator geometrical features (e.g. tabs, rings etc.) to improve the effectiveness and likelihood of electrolyte contact under the target application conditions.

The separator materials illustrated in FIGS. 12A-12C incorporate continuous separator geometry of graduated glass density to optimize the capillary attractive forces to draw electrolyte from the reservoir with the minimum amount of glass material. A laser may be used to produce an array of "holes" or ablate material from the target surface to modify the glass density locally.

FIG. 12A illustrates a first example of material comprising holes 1202 (or removed material), wherein the geometry of the holes 1202 varies along the length of the material, thereby varying the density of the material along the length. A first section 1204 may comprise a first pattern of holes 1202. A second section 1206 may comprise a second pattern of holes 1202, wherein the holes 1202 of the second pattern are spaced further apart than the first pattern. A third section 1208 may comprise solid material, where no holes have been created in the material. In the example shown in FIG. 12A, the density of the material may increase from the first section 1204 to the second section 1206, and may increase from the second section 1206 to the third section 1208.

FIG. 12B illustrates a second example of material comprising holes 1212 (or removed material), wherein the geometry of the holes 1212 varies along the length of the material, thereby varying the density of the material along the length. A first section 1214 may comprise a first pattern of holes 1212. A second section 1216 may comprise a second pattern of holes 1212, wherein the holes 1212 of the second pattern are spaced further apart than the first pattern. A third section 1218 may comprise solid material, where no holes have been created in the material. In the example shown in FIG. 12B, the density of the material may increase from the first section 1214 to the second section 1216, and may increase from the second section 1216 to the third section 1218.

FIG. 12C illustrates a third example of material comprising holes 1222 (or removed material), wherein the geometry of the holes 1222 varies along the length of the material, thereby varying the density of the material along the length. A first section 1224 may comprise a first pattern of holes 1222. A second section 1226 may comprise a second pattern of holes 1222, wherein the holes 1222 of the second pattern are spaced further apart than the first pattern. A third section 1228 may comprise solid material, where no holes have been created in the material. In the example shown in FIG. 12C, the density of the material may increase from the first section 1224 to the second section 1226, and may increase from the second section 1226 to the third section 1228, though the density of the separator material can increase or decrease in any order in adjacent sections. Additionally, lateral variations across the width of the separator may be incorporated, where the same principles as defined here can be used in any combination in the XY plane of the separator.

FIGS. 12A-12C illustrate examples of how the density of a material may be varied along the length of the material. In some cases, the variation may be measured by percentage of material removed. In some cases, the variation may be measured by percentage of material remaining. Multiple patterns of holes may be utilized in one separator, wherein the patterns may be located strategically along the separator to create variations in density along the separator. The variations in glass density can be leveraged to improve electrolyte diffusion through the sensor. Where an electrolyte "reservoir" is required, it is beneficial to minimize the glass density so that the maximum free volume is realized that can be completely accessed by remaining glass fibers.

The holes in the material may be created using a laser cutter. For example, a $CO_2$ laser cutter may be used with a wave length of approximately 10600 nanometers. The laser cutter may comprise a 370 mm lens which gives a spot size of approximately 540 microns. The laser cutter may comprise an 80 watt air cooled laser.

Reducing the volume of material in defined sections of separator material (which may be GFA) could be achieved using the laser in spot marking mode to add perforations to areas of the GFA. Reducing the volume of material in defined sections of separator material may also be achieved using the laser on different power or speed settings to remove layers of GFA in certain sections.

Figure 13A:
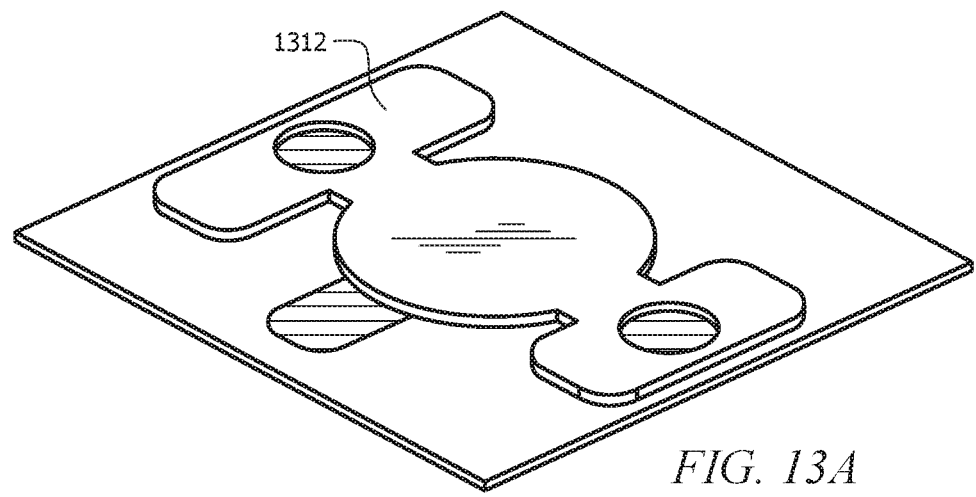
FIGS. 13A-13B illustrate a shaped separator and a planar arrangement of electrodes according to an embodiment.
Figure 13B:
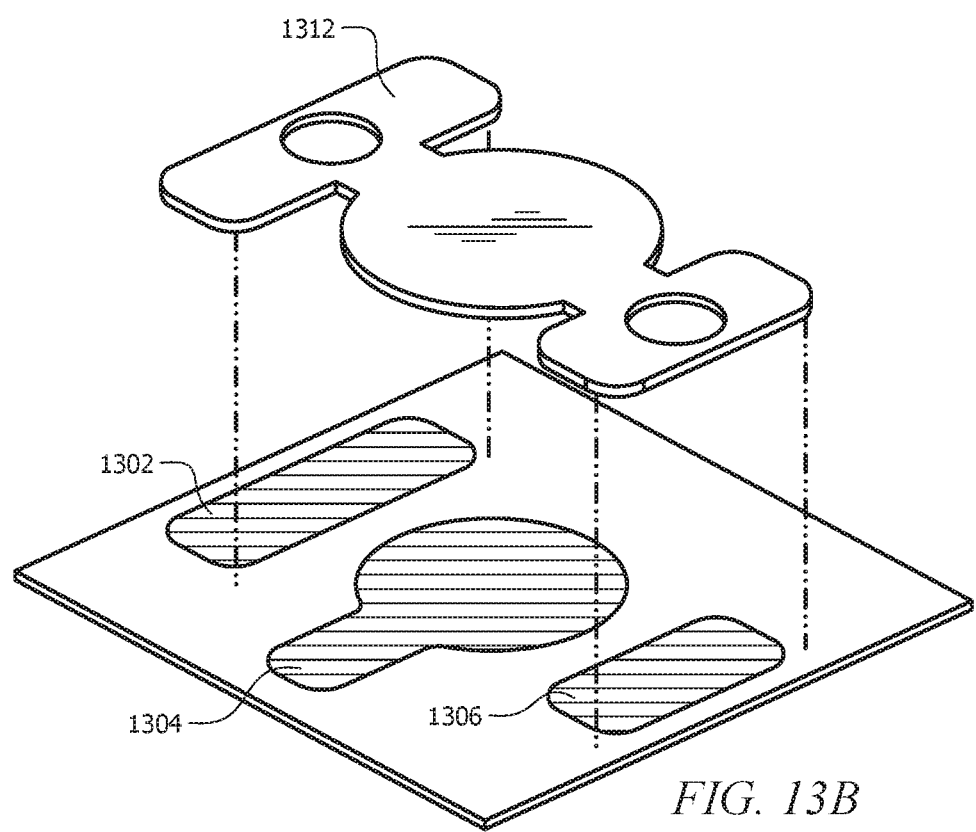

FIGS. 13A and 13B illustrate another example of a shaped separator 1312 that may be used with a planar arrangement of electrodes 1302, 1304 and 1306. The shaped separator 1312 may comprise variations in width, length, and density between the contact points with the electrodes 1302, 1304, 1306. The separator 1312 may use the variations in width to control the amount of electrolyte retention as well as an ion gradient between electrodes 1302, 1304, 1306. For example, sections of the shaped separator 1312 having narrower widths may act as choke points to control the ion concentration gradient between the counter and sensing electrode.

While the above sensor is described in the context of an oxygen sensor, similar concepts and practices could be used in a variety of electrochemical sensors.

Some sensors use three electrodes orientated nominally in a common plane. This configuration allows for a shift of the bias of the effective cross sectional areas of the interfacial phases further towards the liquid/gas (electrolyte/internal "air" reservoir) interfaces rather than the solid/liquid/solid (catalyst/electrolyte/catalyst) interfaces. By designing the geometry of internal components to modify the effective contact areas between the electrolyte and gas phase within the sensor, the local rates of interfacial diffusion of oxygen between the electrolyte and the internal gas volumes can be controlled to improve the electrochemical performance of the electrochemical sensor. This may minimize any "polarization" effects associated with the limiting diffusion rates of dissolved oxygen away from the site of generation at the counter electrode and may prevent the local formation of bubbles or micro-bubbles of gases (typically oxygen and nitrogen) in the electrolyte which can lead to a disturbance in the electrochemistry occurring at the three electrodes, reducing counter electrode (anode) "activity" as a result of the reduction in the effective contact area between the catalyst and electrolyte or producing transients currents at the sensing electrode (cathode).

The inclusion of openings or cavities in internal components of the sensors, referred to hereafter as "breather slots," in the body component of a planar sensor may provide control of the gas exchange between the electrolyte in the separator and the gas phase in the reservoir of the sensor. In other words, the breather slots may provide sufficient contact area between the electrolyte contained in the separator and the gas phase in the reservoir of the sensor to allow for control of the equilibrium between the gases dissolved in the electrolyte and the gas phase. The breather slots may provide gas access to the free space in the reservoir, and may also allow excess free electrolyte (that is not localized elsewhere in the reservoir) to contact the separator directly if the sensor is in the right orientation. Additionally, the breather slots may allow for the electrolyte concentration in portions of the separator material to be controlled, further affecting and controlling the movement of the electrolyte within the separator.

For example, breather slots located near the counter electrode may be operable to vent bubbles (or gases) generated at the electrode into the reservoir, so that the counter electrode may remain wetted by the electrolyte and functioning. The breather slots near the counter electrode may prevent the produced gases from drying out the electrode.

In another example, breather slots located near the reference and/or sensing electrodes may allow for faster exchange of water vapor from the reservoir to the electrodes, where the electrodes may function in dry conditions. The breather slots near the reference and/or sensing electrodes may allow gas from the reservoir to more quickly contact the electrodes. Water transport through the gas phase is orders of magnitude faster than diffusion through a liquid, so localised increases in electrolyte concentraiton due to drying out are better managed by allowing gas phase access of water to the dried regions, rather than requiring it to diffuse through the electrolyte itself from wetter parts.

Electrochemical oxygen pump sensors can employ three electrodes that operate in an electrolyte having different concentrations of dissolved oxygen in intimate contact with the electrocatalyst. To improve the electrochemical reactions occurring at all electrodes, any constraining concentrations of reactants and products (Le Chatelier's principle) can be reduced within their local environments.

The effective cross sectional areas of the breather slots may be optimized for the specific requirements of each of the electrodes. Around the counter electrode in an oxygen sensor, the cross sectional area of the breather slots may be increased, as it is beneficial to increase the rate of diffusion of a dissolved target gas (such as oxygen) away from the site of generation into the internal sensor reservoir. Around the reference electrode, the cross sectional area of the breather slots may be balanced to control the dissolved target gas concentration in the vicinity of the reference electrode, imparting greater sensor tolerance to external target gas concentrations. Around the sensing electrode, the cross sectional area of the breather slots may be controlled to create an anaerobic zone around the sensing electrode, thereby reducing baseline currents generated in oxygen free environments and also improving the response times to reach baseline conditions.

Referring back to FIG. 2, an exemplary embodiment of breather slots 220 are shown molded into the body 102 near the counter electrode 111, where the cross sectional area of the breather slots may be maximized, as it is beneficial to increase the rate of diffusion of dissolved oxygen away from the site of generation into the internal sensor reservoir. Additionally, in FIG. 3, another exemplary embodiment of breather slots 340 are shown molded into the support table 302 near the counter electrode 310, where the cross sectional area of the breather slots 340 may be maximized, as it is beneficial to increase the rate of diffusion of dissolved oxygen away from the site of generation into the internal sensor reservoir.

While the above sensor is described in the context of an oxygen sensor, similar concepts and practices could be used in a variety of electrochemical sensors.

In order to avoid spiking and glitch issues as described herein, one or more features to control the pressure within the sensor can be used. Such a feature can allow the gas to move from bulk free space of the body as the gas expands or contracts due to pressure and temperature effects. When the electrolyte level in the sensor is at a high level, e.g. when the sensor is new, in a filled state, and/or operated in high relative humidity conditions, it is not likely that there will be spaces connecting into a gas path. Therefore, it is important to ensure that good gas communication is maintained at all times in all orientations.

In an electrochemical sensor, a highly porous breather tab may be used to form a pathway for air contained within the sensor to vent out through the breather tab (in the case of an increase in internal pressure) and/or vent in through the breather tab (in the case of a decrease in internal pressure) via a suitable aperture (capillary or other) in the sensor enclosure to provide gaseous communication between the sensor interior and environment. A sensor may normally contain sources of air or other gases, where gas can be produced by the electrochemical reaction at an electrode (normally the counter electrode), or air can be found in voids between mechanical parts or in the free volume in the reservoir. The breather tab can comprise a hydrophobic yet porous material such as PTFE. The hydrophobic nature of the membrane may reduce the likelihood of a liquid entering the membrane and blocking gas flow. Further, the porous nature of the breather tab can allow gases to flow through the membrane between a surface of the membrane in contact with a gaseous space in the sensor and a surface of the membrane in contact with a vent hole. The hydrophobic nature of the membrane may also aid in preventing any liquid (e.g., the electrolyte) from reaching the vent hole and leaking from the sensor.

If the breather tab is not secured in position by design, or if the sensor takes on water when in a high humidity environment, a vent blockage or partial blockage could be caused by the electrolyte, thereby preventing gas from accessing the breather tab. Also, the sensor may be positioned, either by design or during use, in an orientation which allows the electrolyte to prevent the gas from accessing the breather tab. In some instances, an attachment (such as a heat stake or other connection between the breather tab and the housing) can block or partially block the vent by compressing and thus restricting the air flow through the breather tab. This may prevent a gas from flowing between an access surface on the membrane to a vent located on an opposite side of the attachment point.

If a vent is blocked or expanding air within the sensor cannot access the vent, oxygen or other gas can find its way to one of the other electrodes and create a spike in the sensor output. This spiking can cause issues for the user of the sensor by creating false alarms. It is possible to arrange the breather tab so that it can be positioned to access the gas produced at the counter electrode, in voids and the gas in the reservoir, in a repeatable way which will remain so during the sensor's life.

Figure 14:
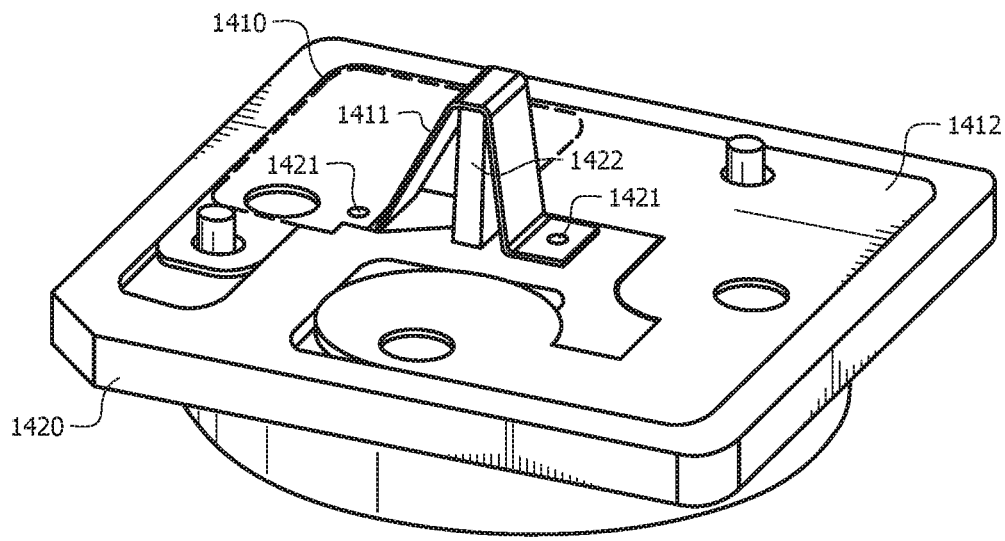
FIG. 14 illustrates a breather tab used in an electrochemical gas sensor according to an embodiment.

Referring now to FIG. 14, a counter electrode 1410 is made from a PTFE tape which allows gas to pass laterally through its structure. The counter electrode 1410 may be partially covered by a separator 1412 (and thereby shown in dashes). In FIG. 14, a portion of the counter electrode 1410 may function as a breather tab 1411 for the sensor. The breather tab 1411 may be attached (via heat stakes 1421) to the cap 1420 where the breather tab 1411 (of the counter electrode 1410) bridges over a protrusion 1422 from the cap 1420. The heat stake 1421 is small enough not to affect the venting properties and may be located at or near the end of the breather tab 1411. Attaching the breather tab 1411 to the cap 1420 and bridging over the plastic protrusion 1422 allows the breather tab 1411 to be retained in a fixed position and orientation for the life of the sensor.

Figure 15:
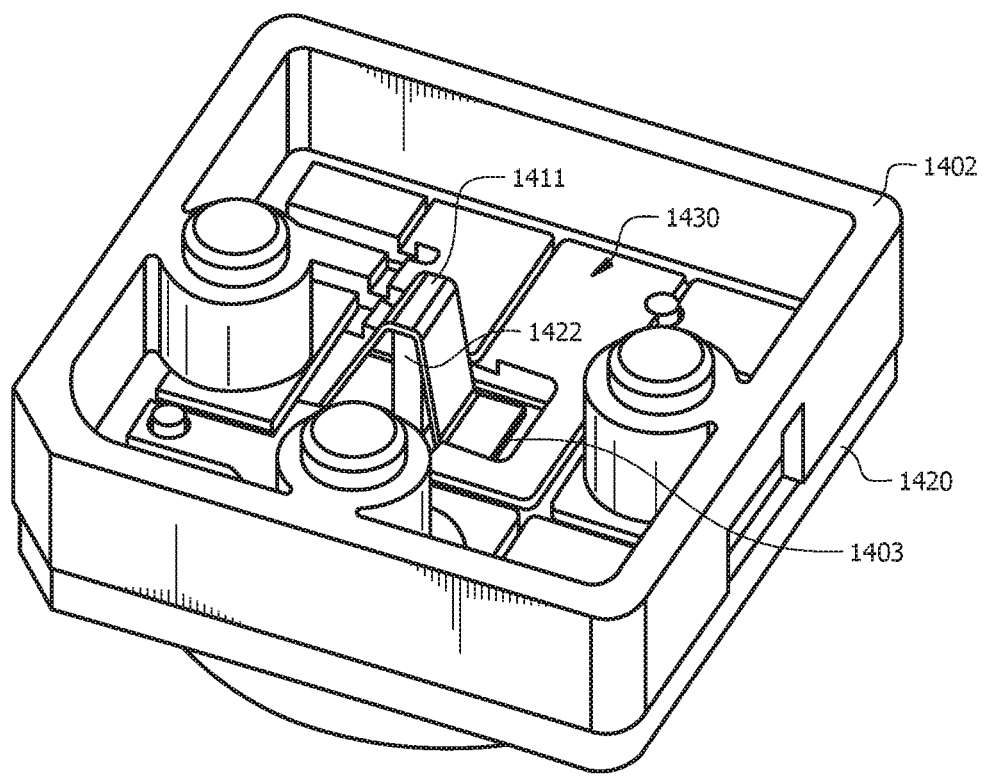
FIG. 15 illustrates another view of the breather tab used in an electrochemical gas sensor according to an embodiment.

In FIG. 15, a table 1402 may be attached over the separator 1412 (shown in FIG. 14), where the table 1402 creates a reservoir 1430. The table 1402 may comprise an opening 1403 for the protrusion 1422. The breather tab 1411 may be routed over the protrusion 1422 so it traverses the reservoir 1430 and it is part of the counter electrode 1410. This allows gas to access the breather tab 1411 in any orientation of the sensor, even in high humidity when the level of electrolyte within the reservoir 1430 is high. The sensor elements illustrated in FIGS. 14-15 may be assembled in one direction, making it easy to manufacture.

Figure 16:
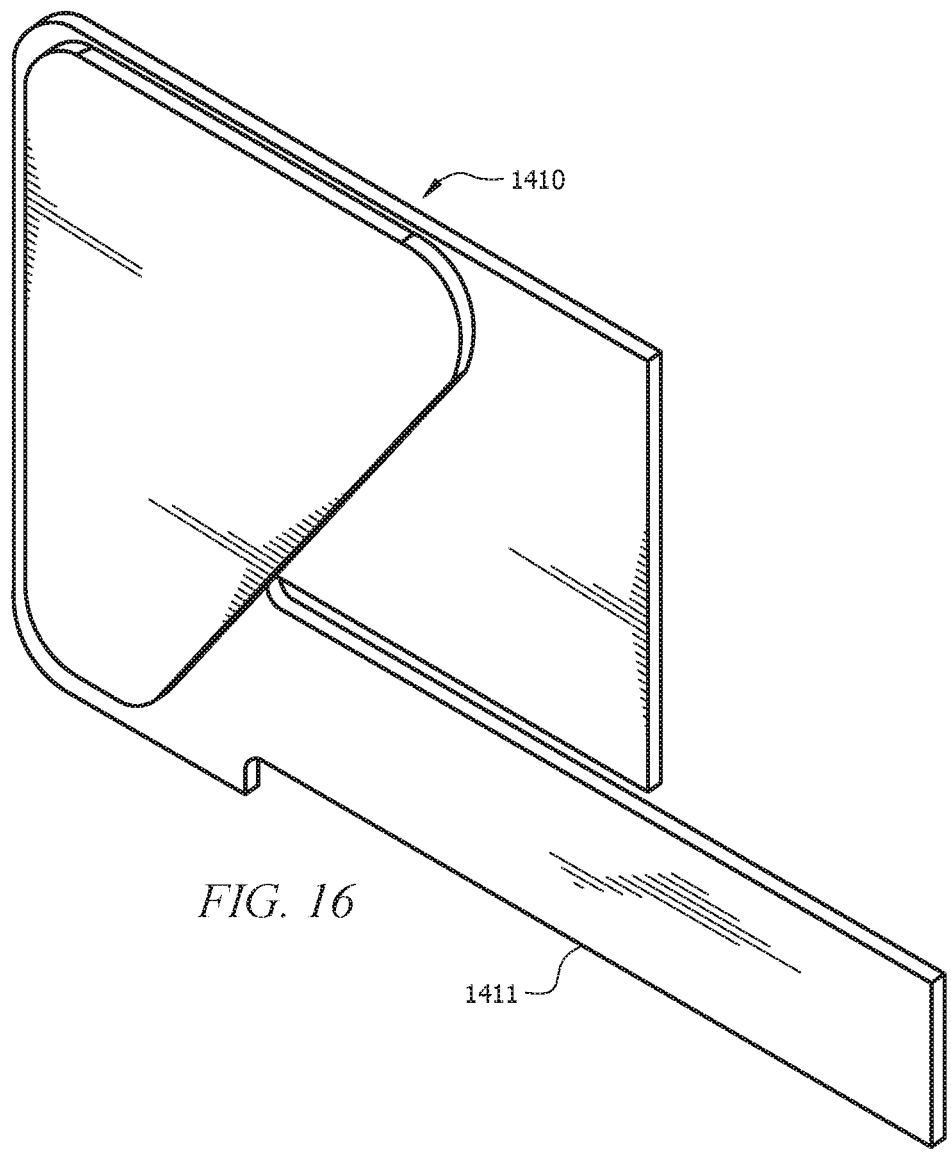
FIG. 16 illustrates a counter electrode and breather tab according to an embodiment.

FIG. 16 shows the counter electrode 1410 comprising the breather tab 1411, where the breather tab 1411 is operable to fold over the protrusion (shown above) and be heat staked in place. A vent hole can be disposed in the housing adjacent the counter electrode 1410 to allow any gases to pass through the length of the breather tab 1411 and exit and/or enter the sensor through the vent hole. The counter electrode 1410 can be formed directly on the breather tab 1411, wherein the breather tab can form the backing tape for the deposition of the catalytic material forming the counter electrode 1410.

Figure 17:
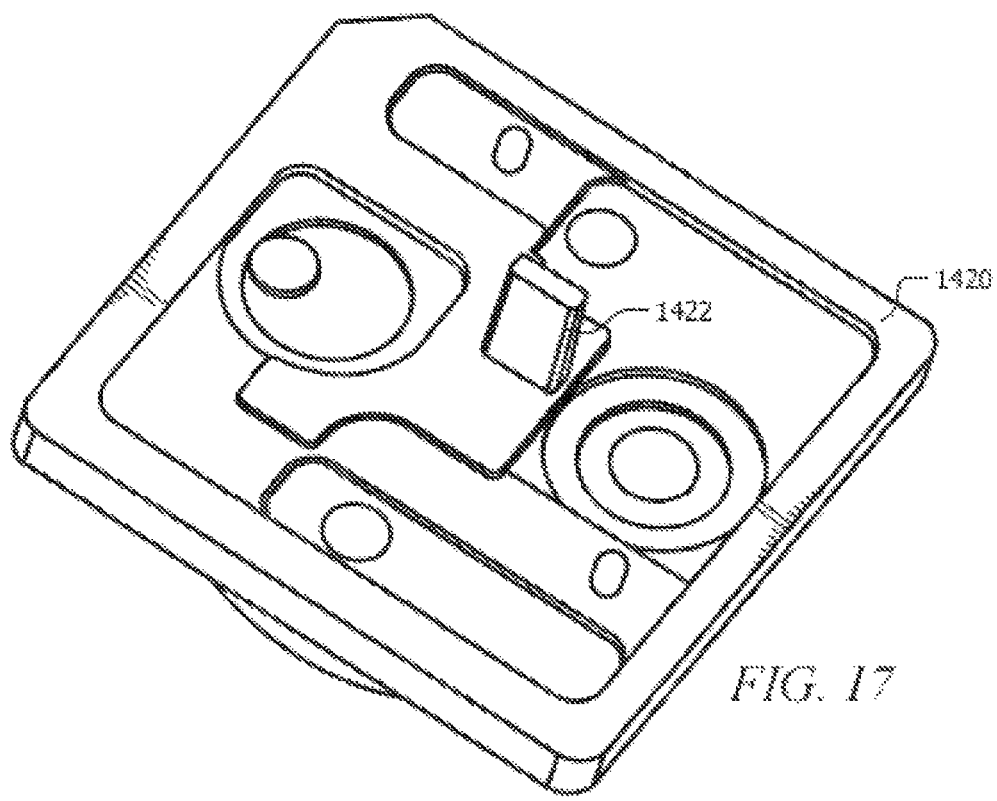
FIG. 17 illustrates a housing comprising a protrusion according to an embodiment.
Figure 18:
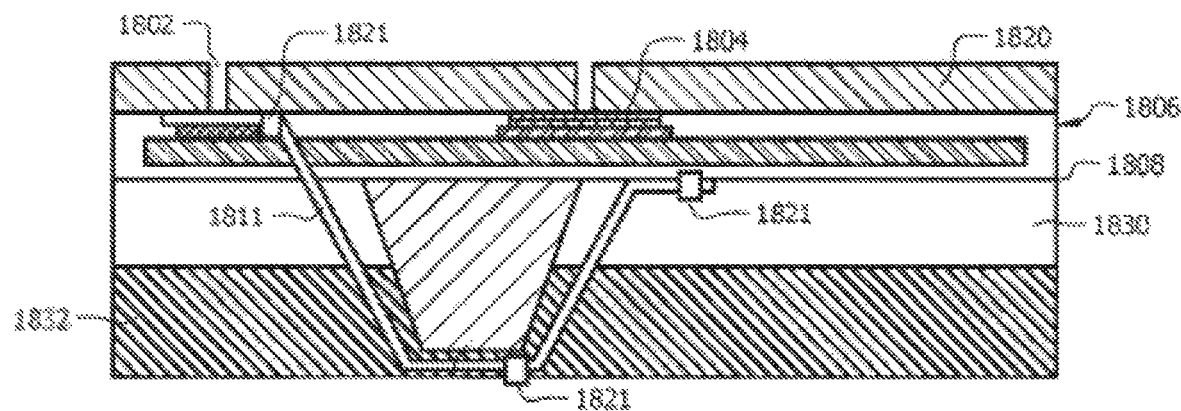
FIG. 18 illustrates a cross-sectional view of an electrochemical gas sensor comprising a breather tab according to an embodiment.

FIG. 17 shows a detailed view of the cap 1420 and protrusion 1422. FIG. 18 further illustrates the use of the breather tab 1811 located within the reservoir 1830. The breather tab 1811 may be positioned such that it is not fully covered by the electrolyte 1832 in any orientation. The breather tab 1811 may be in direct contact with the vent hole 1802, and may extend into the center of the reservoir 1830. The vent hole 1802 may be sealed from the interior elements of the sensor (e.g. electrolyte 1832) based on the hydrophobic properties of the breather tab 1811.

The breather tab 1811 may comprise one continuous piece of highly porous PTFE to enable continuous lateral movement of gas though its full length. The breather tab 1811 may extend outwards in one dimension from the vent 1802 and extend down away from the vent 1802 through the full length of the reservoir 1830. The breather tab 1811 may then extend back up to the base/table 1808 under the electrode compartment 1806. The breather tab 1811 may be secured in one or more locations by heat sealing 1821 to ensure it does not move during operation.

Figure 19:
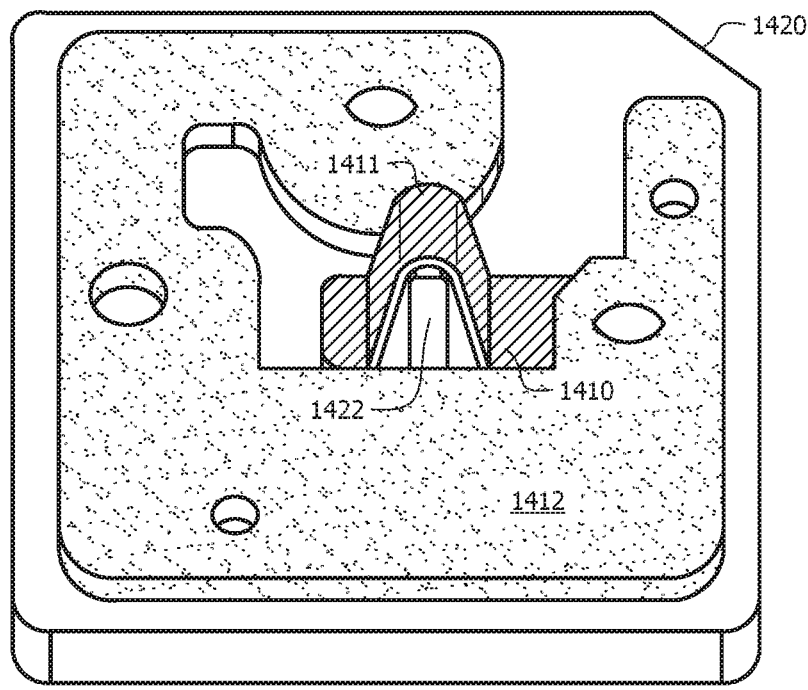
FIG. 19 illustrates another view of an electrochemical gas sensor comprising a breather tab according to an embodiment.
Figure 20:
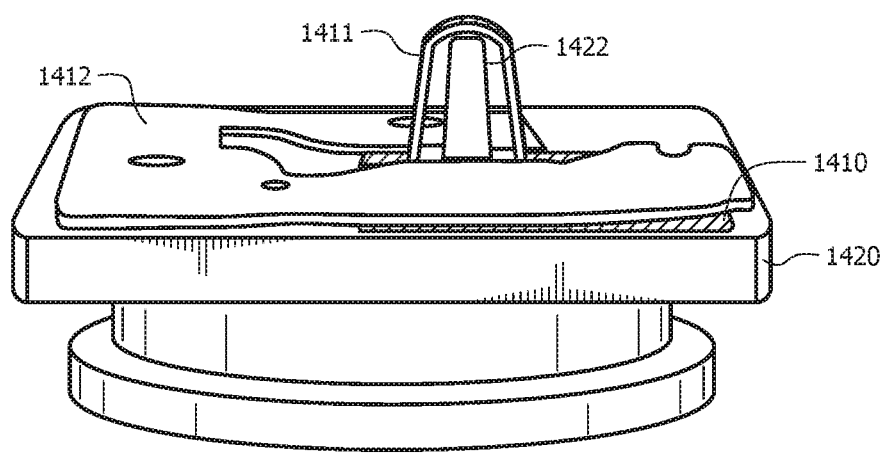
FIG. 20 illustrates yet another view of an electrochemical gas sensor comprising a breather tab according to an embodiment.

FIGS. 19 and 20 show additional views of the cap 1420 comprising the protrusion 1422, the separator 1412, the counter electrode 1410, and the breather tab 1411 described in FIGS. 14 and 15.

While the above sensor is described in the context of an oxygen sensor, similar concepts and practices could be used in a variety of electrochemical sensors.

Embodiments of the disclosure include an electrochemical sensor comprising a housing defining a reservoir; a sensing electrode; a counter electrode; at least one separator retaining an electrolyte, wherein the electrolyte provides an ionically conductive pathway between each of the sensing electrode and the counter electrode within the housing; and a plurality of channels located on the interior of the reservoir, operable to transport electrolyte from the reservoir into the separator.

In an embodiment of the electrochemical sensor, the channels are small enough to create a capillary effect within the channels. In an embodiment of the electrochemical sensor, when the level of electrolyte is low, the electrolyte is localized at the reservoir walls by the channels and then moved by the channels toward the separator. In an embodiment of the electrochemical sensor, the channels comprise a plurality of ridges between raised portions located along the base of the reservoir. In an embodiment of the electrochemical sensor, the sensor may further comprise a plurality of pins operable to contact the electrodes, wherein the pins are located within bosses attached to the housing. In an embodiment of the electrochemical sensor, the channels comprise narrow corners at the attachment point between the housing and the bosses. In an embodiment of the electrochemical sensor, the channels comprise a plurality of channels between raised portions located along the base of the reservoir, and wherein the channels are operable to direct the electrolyte toward the narrow corners. In an embodiment of the electrochemical sensor, when the level of electrolyte is low, the electrolyte is localized at the reservoir walls by the channels and then moved by the narrow corners toward the separator. In an embodiment of the electrochemical sensor, the channels comprise a width of approximately 250 micrometers ($\mu$m). In an embodiment of the electrochemical sensor, the channels comprise a width of approximately 300 $\mu$m. In an embodiment of the electrochemical sensor, the channels comprise a width between approximately 200 $\mu$m and 400 $\mu$m. In an embodiment of the electrochemical sensor, the channels comprise a width between approximately 100 $\mu$m and 500 $\mu$m. In an embodiment of the electrochemical sensor, the channels comprise a width less than approximately 500 $\mu$m. In an embodiment of the electrochemical sensor, the channels comprise a depth of approximately 500 $\mu$m. In an embodiment of the electrochemical sensor, the channels comprise a depth less than approximately 600 $\mu$m.

Embodiments of the disclosure include a method for transporting electrolyte within an electrochemical sensor comprising providing a housing defining a reservoir; forming channels on the interior walls of the reservoir, wherein the channels are small enough to create a capillary effect within the channels; and placing liquid electrolyte within the reservoir, wherein the channels transport the liquid electrolyte through the reservoir toward a separator within the electrochemical sensor.

In an embodiment of the method, when the level of electrolyte is low, the electrolyte is localized at the reservoir walls by the channels and then moved by the channels toward the separator. In an embodiment of the method, forming channels on the interior walls of the reservoir comprises forming bosses attached to the housing, wherein the bosses are operable to surround one or more pins, and wherein the channels comprise narrow corners at the attachment point between the housing and the bosses. In an embodiment of the method, forming channels on the interior walls of the reservoir comprises forming a plurality of channels between raised portions located along the base of the reservoir, and wherein the channels are operable to direct the electrolyte toward the narrow corners. In an embodiment of the method, when the level of electrolyte is low, the electrolyte is localized at the reservoir walls by the channels and then moved by the narrow corners toward the separator.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of, consisting essentially of, and comprised substantially of. Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. An electrochemical sensor comprising:
a housing having interior walls defining a reservoir;
a sensing electrode;
a counter electrode located in a common plane with the sensing electrode;
at least one separator retaining an electrolyte, wherein the electrolyte provides an ionically conductive pathway between the sensing electrode and the counter electrode,
wherein the housing comprises:
a plurality of channels located along a base of the reservoir, configured to transport the electrolyte towards the interior walls and localize the electrolyte at the interior walls; and
a plurality of corners located along the interior walls of the reservoir, configured to transport and direct the localized electrolyte from the reservoir towards the at least one separator at or near a contact point between the at least one separator and one or more contact pins, wherein the plurality of corners are located at one or more vertical corners of one or more bosses located within the housing, wherein the one or more bosses surround the one or more contact pins.

2. The electrochemical sensor of claim 1, wherein, when a level of electrolyte is low, the electrolyte is localized at the interior walls by the plurality of channels and then moved by the plurality of corners toward the at least one separator.

3. The electrochemical sensor of claim 1, wherein the plurality of corners are positioned between the base of the reservoir and the at least one separator.

4. The electrochemical sensor of claim 1, wherein the plurality of channels and the plurality of corners comprise at least three-sided channels configured to move the electrolyte located within the housing upward toward the at least one separator.

5. The electrochemical sensor of claim 1, wherein the plurality of channels comprise ridges located along the base of the reservoir configured to direct the electrolyte to flow to the corners of the one or more bosses, and wherein the plurality of corners direct the electrolyte upward, via capillary forces at the corners, into the at least one separator.

6. The electrochemical sensor of claim 1, wherein, when a level of electrolyte is low, the electrolyte is localized at the interior walls by the plurality of channels and then moved by the plurality of corners toward the at least one separator.

7. The electrochemical sensor of claim 1, wherein the plurality of corners comprises one or more vertical ridges located along a side of the interior walls of the housing.

8. The electrochemical sensor of claim 1, wherein one or more surfaces of the plurality of channels and/or the plurality of corners are surface treated to direct fluid flow within the plurality of channels and plurality of corners.

9. The electrochemical sensor of claim 1, wherein the plurality of channels are not sized to create a capillary effect.

10. The electrochemical sensor of claim 1, further comprising a table located between the at least one separator and the reservoir, wherein the table comprises one or more indentations configured to allow contact between the plurality of corners and the at least one separator.

11. The electrochemical sensor of claim 10, wherein the table comprises additional wicking channels configured to direct electrolyte toward the one or more indentations.

12. The electrochemical sensor of claim 1, wherein the plurality of channels and plurality of corners comprise a width less than 500 µm.

13. The electrochemical sensor of claim 1, wherein the plurality of channels and plurality of corners comprise a depth less than 600 µm.

14. A method for transporting electrolyte within an electrochemical sensor, the method comprising:
  providing a sensing electrode and a counter electrode, wherein the sensing electrode and the counter electrode are located on a common plane;
  providing a housing having interior walls defining a reservoir;
  forming corners on the interior walls of the reservoir, wherein the corners are sized to create a capillary effect;
  forming channels in a base of the reservoir, wherein the channels are configured to transport electrolyte within the reservoir toward the corners;
  assembling the housing with at least one separator and a plurality of electrodes in contact with the at least one separator; and
  placing liquid electrolyte within the reservoir, wherein the at least one separator is configured to retain the electrolyte, wherein the electrolyte provides an ionically conductive pathway between the plurality of electrodes, and wherein the corners and channels transport the liquid electrolyte from the reservoir toward the at least one separator at or near a contact point between the at least one separator and one or more contact pins, wherein the corners are located at one or more vertical corners of one or more bosses located within the housing, and wherein the one or more bosses surround the one or more contact pins.

15. The method of claim 14, wherein, when a level of electrolyte is low, the electrolyte is localized at the interior walls by the channels.

16. The method of claim 14, wherein the forming corners on the interior walls of the reservoir comprises forming the one or more bosses attached to the housing, wherein the corners are defined at an attachment point between the housing and the one or more bosses.

17. The method of claim 16, wherein the forming channels on the interior walls of the reservoir comprises forming a plurality of channels between raised portions located along the base of the reservoir, and wherein the channels are configured to direct the electrolyte towards the corners.

18. The method of claim 16, wherein, when a level of electrolyte is low, the electrolyte is localized at the interior walls by the channels and then moved by the corners toward the at least one separator.

* * * * *